(12) United States Patent
Bento et al.

(10) Patent No.: US 12,397,198 B1
(45) Date of Patent: Aug. 26, 2025

(54) PERSONALIZED COMMUNICATION IN A DIGITAL THERAPY PLATFORM

(71) Applicant: Sword Health, S.A., Oporto (PT)

(72) Inventors: Virgílio António Ferro Bento, Oporto (PT); Ivo Emanuel Marques Gabriel, Oporto (PT); Luís Ungaro Pinto Coelho, Oporto (PT); Daniela Alves do Paço, Oporto (PT); Helena Isabel Melo dos Santos, Oporto (PT); Manuel João Fernandes Silva, Oporto (PT); Kathryn Leigh Dailey, Bend, OR (US)

(73) Assignee: SWORD HEALTH, S.A., Oporto (PT)

( * ) Notice: Subject to any disclaimer, the term of this patent is extended or adjusted under 35 U.S.C. 154(b) by 0 days.

(21) Appl. No.: 18/585,355

(22) Filed: Feb. 23, 2024

(51) Int. Cl.
| | |
|---|---|
| A63B 24/00 | (2006.01) |
| G16H 10/60 | (2018.01) |
| G16H 20/30 | (2018.01) |
| G16H 80/00 | (2018.01) |

(52) U.S. Cl.
CPC ...... *A63B 24/0062* (2013.01); *A63B 24/0003* (2013.01); *G16H 10/60* (2018.01); *G16H 20/30* (2018.01); *G16H 80/00* (2018.01); *A63B 2024/0009* (2013.01); *A63B 2024/0068* (2013.01)

(58) Field of Classification Search
CPC ............ A63B 24/0062; A63B 24/0003; A63B 2024/0009; A63B 2024/0068; G16H 10/60; G16H 20/30; G16H 80/00
See application file for complete search history.

(56) References Cited

U.S. PATENT DOCUMENTS

| | | |
|---|---|---|
| 9,898,789 B2 | 2/2018 | Ram et al. |
| 10,130,311 B1 | 11/2018 | De Sapio et al. |
| 10,413,238 B1 * | 9/2019 | Cooper .................. G16H 40/67 |

(Continued)

FOREIGN PATENT DOCUMENTS

| | | |
|---|---|---|
| CN | 115023763 A | 9/2022 |
| WO | WO-2015103442 A1 | 7/2015 |
| WO | WO-2019010435 A1 | 1/2019 |

OTHER PUBLICATIONS

U.S. Appl. No. 18/585,380, filed Feb. 23, 2024, Personalized Recommendations in a Digital Therapy Platform.
(Continued)

*Primary Examiner* — Sundhara M Ganesan
(74) *Attorney, Agent, or Firm* — SCHWEGMAN LUNDBERG & WOESSNER, P.A.

(57) ABSTRACT

An example digital therapy platform is disclosed that provides personalized, real-time feedback to patients during sessions. The platform collects real-time performance data during the sessions, including metrics such as range of motion, pelvic floor movements, exercise completion rates, and the accuracy of movements. The digital therapy platform may also retrieve historical data from past sessions to provide a comprehensive overview of the patient's context. The digital therapy platform dynamically generates structured prompts based on the analyzed data and provides these prompts to a large language model (LLM). The LLM generates personalized messages tailored to the patient's specific context. The digital therapy platform delivers the personalized messages to the patient through a user interface.

20 Claims, 12 Drawing Sheets

(56) References Cited

U.S. PATENT DOCUMENTS

| | | | |
|---|---|---|---|
| 11,039,763 B2* | 6/2021 | Ye | A61B 5/1118 |
| 2007/0179816 A1* | 8/2007 | Lemme | G16H 20/30 |
| | | | 482/8 |
| 2012/0290319 A1* | 11/2012 | Saria | G16H 15/00 |
| | | | 705/3 |
| 2015/0038806 A1 | 2/2015 | Kaleal, III et al. | |
| 2015/0324532 A1* | 11/2015 | Jones | G16H 40/67 |
| | | | 705/2 |
| 2018/0330810 A1 | 11/2018 | Gamarnik et al. | |
| 2019/0328322 A1* | 10/2019 | Inada | G16H 20/60 |
| 2020/0066390 A1* | 2/2020 | Svendrys | G06F 3/0346 |
| 2020/0114207 A1* | 4/2020 | Weldemariam | H04L 51/02 |
| 2021/0202103 A1* | 7/2021 | Bostic | G16H 50/80 |
| 2022/0016484 A1 | 1/2022 | Bissonnette et al. | |
| 2022/0076666 A1 | 3/2022 | Trehan | |
| 2022/0208385 A1 | 6/2022 | Voschina et al. | |
| 2022/0246268 A1* | 8/2022 | Hunter | G16H 40/67 |
| 2022/0392611 A1* | 12/2022 | Appelbaum | H04L 67/12 |
| 2023/0071274 A1 | 3/2023 | Trehan | |

OTHER PUBLICATIONS

"U.S. Appl. No. 18/585,380, Non Final Office Action mailed Apr. 22, 2024", 25 pgs.

U.S. Appl. No. 18/585,380, Advisory Action mailed Oct. 9, 2024, 3 pgs.

U.S. Appl. No. 18/585,380, Examiner Interview Summary mailed Jul. 26, 2024, 2 pgs.

U.S. Appl. No. 18/585,380, Final Office Action mailed Aug. 9, 2024, 23 pgs.

U.S. Appl. No. 18/585,380, Response filed Jul. 22, 2024 to Non Final Office Action mailed Apr. 22, 2024, 19 pgs.

U.S. Appl. No. 18/585,380, Response filed Sep. 30, 2024 to Final Office Action mailed Aug. 9, 2024, 15 pgs.

U.S. Appl. No. 18/585,380, Non Final Office Action mailed Jan. 29, 2025, 20 pgs.

U.S. Appl. No. 18/585,380, Response filed Nov. 8, 2024 to Advisory Action mailed Oct. 9, 2024, 17 pgs.

* cited by examiner

PERSONALIZED COMMUNICATION IN A DIGITAL THERAPY PLATFORM

BACKGROUND

The field of digital therapy has seen significant advancements in recent years, particularly with the integration of technology to assist in the rehabilitation and treatment of patients. One of the components of digital therapy is the provision of feedback to patients during exercises, which is helpful for ensuring correct form, preventing injury, and maintaining patient engagement.

Traditionally, motion analysis systems have been employed to monitor and evaluate a patient's movements during therapy sessions. These systems often rely on a set of hardcoded rules that correspond to specific movements and predetermined feedback in the form of audio or text. For example, a system might instruct a patient with messages, such as "Keep your back straight," "Do not bend your elbow," or "Maintain proper pelvic alignment," based on the detection of certain movement patterns or other sensor feedback.

While these systems have provided a foundation for interactive and responsive therapy sessions, such as musculoskeletal rehabilitation sessions or pelvic-floor therapy sessions, they may be limited by their static nature. The feedback provided is often repetitive and lacks personalization, which can lead to a mechanical interaction between the patient and the system. This can result in a less engaging experience for the patient and may even lead to the disregard of the feedback over time.

Furthermore, these systems typically do not take into account the patient's past performance or the context of their current therapy journey. The feedback is usually based solely on the movements detected during a single session, without considering the patient's progress over time or their specific therapy goals.

Another limitation of current systems is their inability to adapt to the nuanced needs of each patient, which may be particularly important in sensitive areas such as pelvic-floor therapy. The hardcoded rules may not account for the complex interplay of movements that a patient might exhibit, and explicitly encoding rules for every possible interaction may simply be impractical. As a result, the feedback may not address deeper nuances, such as compensatory movements that a patient might make during an exercise.

In addition to the content of the feedback, the mode of delivery may also be an area of concern. Many systems provide feedback in text form, which requires the patient to shift their focus away from the exercise to read the feedback, potentially disrupting the flow of the session. While some systems offer audio feedback, it is often generated in advance and lacks real-time adaptability that could enhance the therapy experience.

BRIEF DESCRIPTION OF THE SEVERAL VIEWS OF THE DRAWINGS

In the drawings, which are not necessarily drawn to scale, like numerals may describe similar components in different views. To easily identify the discussion of any particular element or act, the most significant digit or digits in a reference number refer to the figure number in which that element is first introduced. Some non-limiting examples are illustrated in the figures of the accompanying drawings in which.

DETAILED DESCRIPTION

Figure 1:
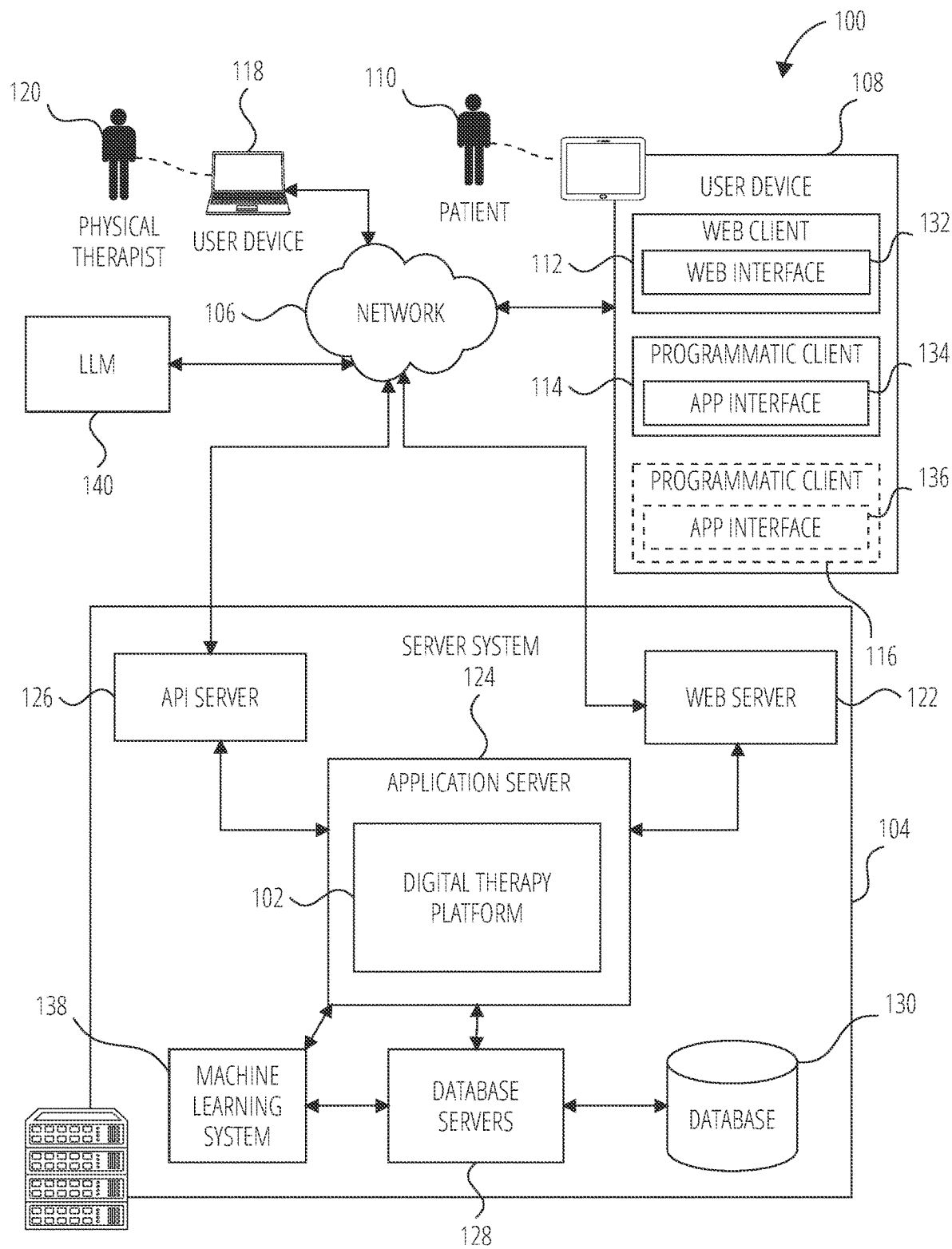
FIG. 1 diagrammatically illustrates a networked computing environment that includes a digital therapy platform, according to some examples.

The present disclosure uses the terms "digital therapy," "digital therapy platform," "patient," "therapist," and "therapy session." As used herein, the term "digital therapy" may include a broad spectrum of health and wellness therapies, interventions, plans, programs, or activities delivered at least partially through digital means. Digital therapy may be aimed at addressing or diagnosing specific conditions and/or aimed at promoting physical fitness or well-being and/or aimed at preventative care. Accordingly, digital therapy may include targeted therapeutic plans, such as those for Musculoskeletal (MSK) rehabilitation, pelvic-floor therapy, or behavioral therapy, but may also include more general activities that are not necessarily linked to a specific therapeutic condition, such as general fitness-related exercises, strength exercises, or injury prevention. Digital therapy programs may be personalized and interactive, where activities are tailored to an individual's health objectives, whether for specific therapeutic purposes or more general purposes (such as fitness enhancement).

As used herein, the term "digital therapy platform" may include to a technology-based or technology-driven platform designed to facilitate one or more health-related and/or wellness-related activities. As mentioned above with reference to "digital therapy," activities associated with a digital therapy platform may be aimed at addressing or diagnosing specific conditions and/or aimed at promoting physical fitness or well-being and/or aimed at preventative care. Accordingly, utilization of a digital therapy platform is not necessarily limited to diagnosing, treating, or managing specific conditions, as it may also be used for general or regular exercise (for example). A digital therapy platform may integrate or leverage various digital tools, such as mobile applications, web applications, wearable devices, motion trackers, other sensors, and/or interactive software to provide personalized solutions.

As used herein, the term "patient" may include a person making use of digital therapy or a digital therapy platform to facilitate health and/or wellness, whether generally or to address a specific condition or concern. A patient may be a person who engages with a digital therapy platform to seek guidance, support, or interventions. A patient may have a specific medical condition that needs to be addressed, or may utilize digital therapy for more general purposes or regular exercise. For example, a patient may be a person who utilizes the digital therapy platform for MSK rehabilitation through a targeted digital therapy program that includes exercises aimed at rehabilitating the person, or a person who utilizes the digital therapy platform to improve general fitness levels, without having a targeted digital therapy program assigned to them.

As used herein, the term "therapist" may include a therapist (e.g., a physical therapist), clinician, physician, other healthcare professional, or worker (e.g., a personal trainer) that treats, manages, communicates with, or otherwise assists with advising, guiding, motivating, treating, or rehabilitating a patient in a digital therapy context. For example, in the context of the present disclosure, a therapist can be a person assigned to work with a patient by offering advice, designing or adapting digital therapy programs, and/or providing motivation and support. In some examples, a therapist involved with a digital therapy platform can have multiple patients assigned to them.

In the context of digital therapy or a digital therapy platform, the term "therapy session" (or simply "session"), as used herein, may include a patient/user engagement with the digital therapy platform. An engagement may involve the patient performing one or more exercises based on instructions or guidance provided by the digital therapy platform, in which case the session can be referred to as an exercise session. A session may be tailored to address a specific health condition (e.g., through targeted exercises). In some cases, a session may be aimed at supporting general wellness, prevention, or fitness goals, without being targeted to a specific condition. Accordingly, a session may involve targeted or general exercises, depending on a patient's needs or requirements. For example, a therapy goal of a patient might be to address or alleviate a specific medical condition, or simply to improve overall health or well-being.

Examples described herein provide a system that can offer more personalized, context-aware, and engaging feedback to patients, thereby improving the effectiveness of digital therapy sessions. Examples of a digital therapy platform are engineered to facilitate an interactive digital therapy session. Such digital therapy platforms provide functionality to engage with patients through automated and computer-generated messages, which are helpful in guiding, motivating, and supporting patients through their therapeutic exercises.

The digital therapy platform, according to some examples, is designed with the understanding that effective therapy extends beyond the mere execution of physical movements; it benefits from a continuous dialogue between the therapist and the patient. This dialogue encompasses not only instructions and corrections but also encouragement and acknowledgment of progress. To provide this aspect of therapy in a digital environment, the digital therapy platform is equipped with communication modules capable of delivering timely and relevant messages at multiple instances throughout a therapy session.

For example, the interaction may begin the moment a patient initiates a session, where the digital therapy platform greets the patient and sets the tone for the upcoming activities. Recognizing the importance of a strong start, in some examples, the digital therapy platform delivers an initial message that is both welcoming and invigorating, aiming to boost the patient's morale and readiness for the session. This initial interaction is helpful as it establishes a rapport with the patient, laying the groundwork for a trusting and responsive relationship.

As the session progresses, the digital therapy platform may continue to interact with the patient by providing real-time feedback after each exercise. This feedback is not a mere regurgitation of data but a synthesis based on the patient's performance, tailored to their specific therapeutic needs and goals. Such personalized communication may be rooted in computational algorithms performed by a system as described herein, which analyze the patient's movements and generate appropriate responses that not only guide the patient through the correct execution of exercises but also provide encouragement and constructive feedback.

The end of the session may be marked by an end-of-session message generated by the digital therapy platform. This message may serve as a review of the patient's performance throughout the session, highlighting achievements and areas for improvement. This message may not only provide a summary of the session but also set the stage for subsequent sessions, ensuring continuity in the patient's therapeutic journey.

The following technical description of a digital therapy platform, according to some examples, sets out some of the limitations of traditional hardcoded systems and the advantages of employing large language models (LLMs) to provide a more adaptive, personalized, or engaging patient experience.

In the realm of digital therapy, the integration of LLMs marks a departure from hardcoded systems. The limitations of hardcoded systems are manifold, primarily stemming from an inability to accommodate the intricate and diverse nature of human physiology and the corresponding therapeutic feedback helpful for effective treatment.

Hardcoded systems may operate on a fixed set of predetermined rules that trigger specific feedback responses to particular movements or conditions detected during a therapy session. This rigid framework is inherently constrained and may fail to capture the subtleties and complexities inherent in patient-specific therapeutic interactions. For example, a hardcoded system might be programmed to issue a generic prompt to "maintain a straight posture" whenever a deviation from an idealized spinal alignment is detected. However, this system may lack the nuanced understanding required to discern the underlying causes of such deviations, whether they be compensatory mechanisms due to underlying pain or the manifestation of a habitual posture misalignment (for example). Consequently, the feedback provided is often generic, lacking the personalized touch that is helpful for patient adherence and progress.

The technical impracticality of encoding every conceivable patient interaction into a hardcoded system is a challenge underscored by the vast array of variables present in physical therapy. Each patient's condition, recovery pace, and interaction with the therapy regimen introduce a multitude of factors that may be considered when generating feedback. The task of programming a system to account for every potential variable and outcome may be laborious or simply impractical, given the dynamic nature of physical therapy and the continuous evolution of best practices within the field.

The diversity of messages that a digital therapy system may be required to generate is considerable. Each patient's unique physical characteristics, therapeutic goals, and response to treatment would benefit from a bespoke approach to the delivery of feedback. A hardcoded system's static nature may render it incapable of synthesizing a patient's historical data, real-time performance, and overarching therapy objectives into a coherent and contextually relevant narrative.

Use of a generative machine learning model such as an LLM within a digital therapy platform offers a technical solution to these challenges. LLMs possess the capability to process extensive datasets, interpret the subtleties of a therapy session, and produce feedback that is not only tailored to the patient's immediate performance but also cognizant of their broader therapeutic journey. This processing allows for an interaction that more closely resembles that of a human therapist, providing feedback that is both technically precise and imbued with the motivational and empathetic qualities essential for patient engagement.

According to some examples described herein, a digital therapy platform leverages the capabilities of one or more LLMs to analyze movement statistics and generate personalized feedback for patients. This feedback is not static but is crafted using an LLM to provide tailored messages that consider the patient's performance, including nuances such as the interplay between different degrees of freedom or range of motion in movement.

In some examples, a digital therapy platform employs prompt engineering to describe the task to the LLM, incorporating both movement statistics and relevant past information from the patient's therapy history. This results in feedback that is not only more appropriate to the patient's current session but also motivational, acknowledging improvements and encouraging continued effort.

To maintain the interactive nature of the therapy session, the personalized messages generated by the LLM may then be converted into audio feedback using a text-to-speech algorithm. This allows for real-time auditory communication, enhancing the naturalness of the interaction and enabling the patient to engage in a dialogue with the system by asking questions and receiving responses in natural language.

The digital therapy platform, according to the described examples, thus provides a technical solution that transcends the limitations of conventional motion analysis systems. By using the processing power of a generative machine learning model, such as an LLM, and integrating patient-specific data, the digital therapy platform delivers feedback that is both technically sound and emotionally supportive, thereby fostering a more engaging and effective therapeutic experience.

Networked Computing Environment 100 (FIG. 1)

FIG. 1 is a diagrammatic representation of a networked computing environment 100 in which some examples of the present disclosure may be implemented or deployed. One or more servers in a server system 104 provide server-side functionality via a network 106 to a networked device, in the example form of a user device 108 that is accessed by a first user in the example form of a patient 110. A web client 112 (e.g., a browser) or a programmatic client 114 (e.g., an "app") may be hosted and executed on the user device 108.

In some examples, the user device 108 executes further web clients or programmatic clients, such as the programmatic client 116 shown in broken lines in FIG. 1.

The one or more servers in the server system 104 also provide server-side functionality via the network 106 to a user device 118 of a second user in the example form of a physical therapist 120. Although not shown in FIG. 1, the user device 118 may include a web client or a programmatic client similar to the web client 112 or programmatic client 114 (or the programmatic client 116) of the user device 108.

An Application Programming Interface (API) server 126 and a web server 122 provide respective programmatic and web interfaces to components of the server system 104. An application server 124 hosts or provides a digital therapy platform 102, which may also be referred to as a digital therapy system, and which includes components, modules, or applications.

The user device 108 and the user device 118 can each communicate with the application server 124, for example, via the web interface supported by the web server 122 or via the programmatic interface provided by the API server 126. It will be appreciated that, although a single user device 108 of the patient 110 and a single user device 118 of the physical therapist 120 are shown in FIG. 1, a plurality of other user devices may be communicatively coupled to the server system 104 in some examples. For example, multiple patients may use their respective user devices to access the digital therapy platform 102, and multiple physical therapists may use their respective user devices to access the digital therapy platform 102.

Further, while certain functions are described herein as being performed at either a user device (e.g., web client 112 or programmatic client 114) or the server system 104, the location of certain functionality either within a user device or the server system 104 may be a design choice. For example, it may be technically preferable to deploy particular technology and functionality within the server system 104 initially, but to migrate this technology and functionality to a programmatic client at a later stage (e.g., when the user device has sufficient processing capacity).

The application server 124 is communicatively coupled to one or more database servers 128, facilitating access to one or more information storage repositories (e.g., a database 130). In some examples, the database 130 includes storage devices that store information to be processed or transmitted by the digital therapy platform 102.

The application server 124 accesses application data (e.g., application data stored by the database servers 128 or database 130) to provide one or more applications to the user device 108 and the user device 118 (e.g., via a web interface 132 or an app interface 134).

The digital therapy platform 102 may provide a digital therapy application, or multiple digital therapy applications, to be accessible via the user device 108 or the user device 118. For example, the patient 110 may access a user portal of the digital therapy application to utilize various functionality, such as consulting virtually with the physical therapist 120, receiving a customized digital physical therapy program, receiving details of exercises to perform, interacting with the digital therapy platform 102 (e.g., providing input and receiving automated feedback messages), and reviewing educational content, while the physical therapist 120 may access a therapist portal of the digital therapy application to utilize various functionality, such as consulting virtually with the patient 110, accessing a therapy workflow, tracking and managing patients.

Where multiple digital therapy applications are provided, different aspects of digital therapy may be provided via the respective applications. In some examples, a first application (e.g., the programmatic client 114) is a mobile application that provides an app interface (e.g., the app interface 134) for educational videos, cognitive behavioral therapy (CBT), and a communication channel with physical therapists, while a second application (e.g., the programmatic client 116) is a tablet application that provides access to exercises and an app interface (e.g., the app interface 136) for such purposes. The digital therapy application is referred to herein primarily as a single application for ease of reference and to facilitate understanding of aspects described herein. It will, however, be appreciated that, where this disclosure may refer to a single "digital therapy application" having certain functions, such functions may be performed by a single application or distributed across multiple applications. The digital therapy application, or applications, may be mobile applications, tablet applications, web applications, combinations thereof, or other types of applications.

To access the digital therapy application provided by the digital therapy platform 102, a user may create an account or access an existing account with a service provider associated with the server system 104 (e.g., a digital health services provider). The patient 110 or the physical therapist 120 may, in some examples, access the digital therapy application using a dedicated programmatic client (e.g., the programmatic client 114 and/or 116), in which case some functionality may be provided client-side, and other functionality may be provided server-side.

Data stored in the database 130 may include various motion data, exercise data, performance data, and user data, such as demographic information, clinical history, and records collected from the patients' user devices as well as through interactions with assigned physical therapists. It is noted that any biometric data or personally identifiable information (PII) is captured, collected, or stored upon user approval and deleted on user request. Further, such data may be used for very limited purposes and for those purposes authorized by a user. To ensure limited and authorized use of biometric information or PII, access to this data is restricted to authorized personnel only, if at all. In addition, appropriate technical and organizational measures are implemented to ensure the security and confidentiality of this sensitive information.

The server system 104 may further host a machine learning system 138. The machine learning system 138 may be used to implement one or more aspects of a machine learning pipeline. For example, the machine learning system 138 may include components enabled to train models based on historic patient data, fine-tune models, or deploy models for inference. Various aspects of machine learning pipelines and other AI-related features are described elsewhere, including with reference to FIG. 9 and FIG. 10.

In some examples, the machine learning system 138 leverages one or more internally and/or externally hosted LLMs, such as the LLM 140 depicted in FIG. 1.

An LLM is a machine learning model trained on vast amounts of data to enable it to process inputs and generate language and, in some cases, other types of content to perform a wide range of tasks. An LLM is able to perform these functions due to its large number of parameters (e.g., billions) enabling it to capture, for example, patterns in language.

These LLMs, which may include foundation models such as GPT (Generative Pre-trained Transformer) or BERT (Bidirectional Encoder Representations from Transformers), serve as the core engines for natural language processing tasks within the digital therapy system. The machine learning system 138 leverages these LLMs to perform a variety of functions to support the operation of the digital therapy platform 102. These functions may include the generation of personalized feedback for patients, the interpretation of patient input and queries, and the synthesis of complex medical data into comprehensible reports for healthcare providers.

Foundation LLMs may be pre-trained on vast datasets and possess a broad understanding of language and context. They are capable of generating human-like text and can be applied to a wide range of language tasks without further training. However, for specialized applications such as digital therapy, where the context and content are highly specific, there may be a need to fine-tune an LLM to better suit the particular requirements of the therapy domain.

Fine-tuned LLMs are adapted from foundation models through additional training on a targeted dataset that is specific to the therapy context. This fine-tuning process involves adjusting the model's parameters to optimize its performance for tasks such as understanding medical terminology, interpreting therapy-specific data, and generating motivational messages that align with therapeutic goals. The fine-tuning process enhances the LLM's ability to provide accurate and relevant responses within the specific context of digital therapy.

The machine learning system 138 may employ a combination of internally hosted LLMs for tasks that require rapid processing and data privacy, and externally hosted LLMs for tasks that can benefit from the scalability and computational power of cloud-based services. This hybrid approach allows the digital therapy platform 102 to maintain a balance between performance, cost, and data security.

Furthermore, the machine learning system 138 is designed to be flexible and scalable, enabling the integration of new LLMs (or other generative machine learning models) as they become available or as the needs of the therapy platform evolve. This ensures that the digital therapy platform 102 can continuously improve its services to patients and healthcare providers.

The machine learning system 138 is a dynamic and integrated part of the digital therapy platform 102, utilizing one or more foundation and/or fine-tuned LLMs to provide sophisticated language processing capabilities. For example, the LLM 140 enables the physical therapist 120 to deliver personalized, context-aware, and clinically relevant interactions, thereby enhancing the overall effectiveness of digital therapy sessions.

One or more of the application server 124, the database servers 128, the API server 126, the web server 122, the digital therapy platform 102, or part thereof, may each be implemented in a computer system, in whole or in part, as described below with respect to FIG. 12. In some examples, third-party applications can communicate with the application server 124 via the programmatic interface provided by the API server 126 (or via another channel). For example, a third-party application may support one or more features or functions on a website or platform hosted by a third party, or may perform certain methodologies and provide input or output information to the application server 124 for further processing or publication. For example, the application server 124 may utilize functionality of machine learning models that are hosted by servers external to the server system 104.

The network 106 may be any network that enables communication between or among machines, databases, and devices. Accordingly, the network 106 may be a wired network, a wireless network (e.g., a mobile or cellular network), or any suitable combination thereof. The network 106 may include one or more portions that constitute a private network, a public network (e.g., the Internet), or any suitable combination thereof.

Figure 2:
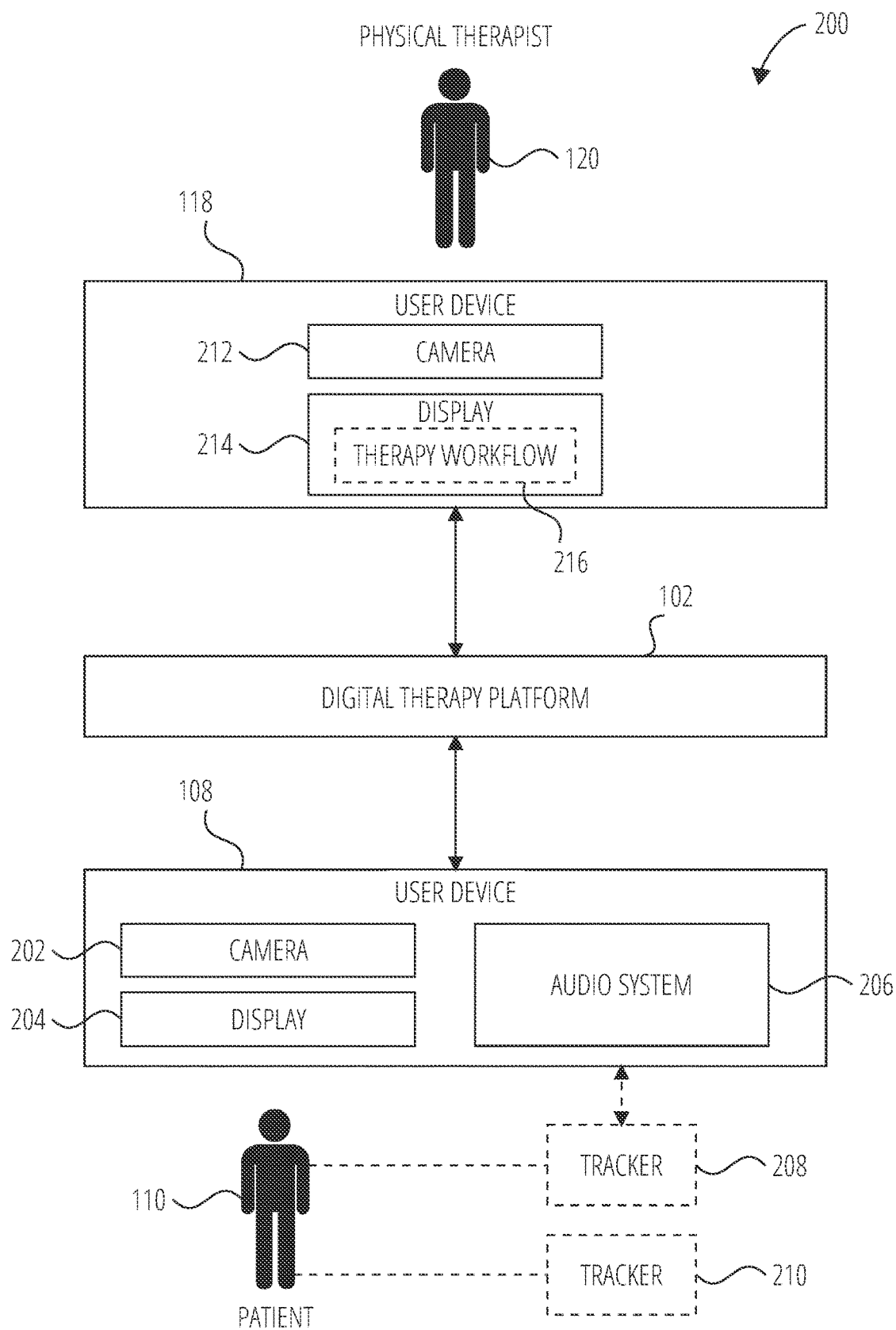
FIG. 2 diagrammatically illustrates interactions between a user device of a physical therapist, a cloud-based digital therapy platform, and a user device of a patient, according to some examples.

Interaction Diagram 200 (FIG. 2)

FIG. 2 shows an interaction diagram 200 depicting interactions between a user device of a physical therapist, the digital therapy platform 102 of FIG. 1, and a user device of a patient, according to some examples. In FIG. 2, the user device 118 of the physical therapist 120 of FIG. 1 and the user device 108 of the patient 110 of FIG. 1 are shown for ease of reference. It will be appreciated that similar interactions may be performed with other user devices connected to the digital therapy platform 102. It will further be understood that only a few selected components of the user device 108 and the user device 118 are shown in FIG. 2 to describe certain functionality, and that the user device 108 and the user device 118 may include numerous other components.

As discussed with reference to FIG. 1, both the user device 108 and the user device 118 are computing devices that can communicate with the digital therapy platform 102 (e.g., by accessing a digital therapy application). The user device 108 and the user device 118 may, for example, be mobile phones, tablets, personal computers, or combinations thereof.

The user device 108 includes, or is connected to, a camera 202, a display 204, and an audio system 206. The user device 108 further includes at least one processor, at least one memory, and a communication module (not shown) for communicating with the digital therapy platform 102 and one or more other devices.

The camera 202 may capture images or video content of the patient 110 performing exercises to allow tracking of user motion via computer vision techniques. For example, identification of anatomical landmarks, measurement of distances, and tracking of body parts may be performed using any computer vision techniques known in the art and they all fall within the scope of the present disclosure. Such computer vision techniques are not described in this document in order not to obscure the invention, but, to name a few non-limiting exemplary digital libraries and algorithms, TensorFlow Pose estimation, MediaPipe Pose, and BlazePose by Google™, and the algorithm described in "Reconstructing 3D Human Pose from 2D Image Landmarks" are some possible computer vision techniques to this end.

The camera 202 and other components of the user device 108 (e.g., microphone, loudspeaker, and communication modules) may also facilitate virtual consultations. The patient 110 may connect with the physical therapist 120 via the digital therapy platform 102, for example, to virtually consult with the physical therapist 120. The display 204 is used to provide a user interface of the digital therapy platform 102, such as a user interface of the digital therapy application.

The audio system 206 may, for example, include one or more microphones and one or more loudspeakers or modules for connecting to external microphones and/or loudspeakers. This enables the patient 110 to provide input to the digital therapy platform 102 in audio format and to receive audio messages from the digital therapy platform 102.

The patient 110 may, for example, enter patient data, such as demographic information, clinical history, and symptoms (e.g., identification of painful zones and pain levels), and the data is then transmitted to the digital therapy platform 102.

The digital therapy platform 102 may generate (e.g., automatically or with assistance from the physical therapist 120) a digital physical therapy program and make it available to the patient 110. For example, the digital therapy platform 102 may guide the patient 110 through an 8-week program or a 12-week program to treat or improve Lower Back Pain (LBP) or another Musculoskeletal (MSK) condition (the actual duration may vary or be dynamic, for example, based on patient condition, engagement, or recovery trajectory).

As mentioned, in some examples, the camera 202 can be used as a tracking sensor. Alternatively, or additionally, the patient 110 may be equipped with trackers 208, 210 on or in their body while performing the exercises forming part of the digital physical therapy program, including those designed for musculoskeletal rehabilitation or pelvic-floor therapy. Each tracker 208, 210 may include at least one sensor, for example, an inertial measurement unit. The inertial measurement unit of each tracker 208, 210 may include one or more inertial sensors selected from, for example, an accelerometer, a gyroscope, or a magnetometer. Sensors may also include one or more force sensors. The inclusion of force sensors is particularly relevant for pelvic-floor therapy, where the measurement of exerted pressure during exercises can provide valuable feedback for the rehabilitation process.

Each tracker 208, 210 may further include at least one processor, at least one memory, and a wireless communications module for communicating with the user device 108. For example, each tracker 208, 210 may transmit advertisement packages, data packets with identification data, data packets with measurements of inertial sensors, data packets with directions computed by the tracker, or combinations thereof. Each tracker 208, 210 may also receive data packets from the user device 108, for example, with tracking instructions. The trackers 208, 210 and/or the user device 108 may run sensor fusion algorithms, for example, to improve accuracy or correct errors in measurements.

Each tracker 208, 210 is adapted to be arranged on or within the body of the patient 110 so that the measurements thereof can be processed by the user device 108 or at the digital therapy platform 102, thereby providing a motion tracking sequence of the person. The trackers 208, 210 may be attached to external body members of the person by means of an attaching device, such as straps, hook-and-loop fasteners, or other means. The trackers 208, 210 or parts thereof may be incorporated into smart watches or other wrist-worn devices. Additionally or alternatively, for therapies such as pelvic-floor therapy, internal sensors, such as intravaginal sensors, may be utilized to measure internal muscular activity and provide precise feedback on exercises specific to this therapy. In some examples, the user device 108 and the trackers 208, 210, including any internal sensors (e.g., a sensor device that is insertable into the pelvic cavity for monitoring during pelvic-floor therapy), form part of a motion tracking kit provided to the patient 110. Each tracker 208, 210, whether external or internal, may be powered by one or more batteries (e.g., a rechargeable battery).

The user device 108 may provide (or cause another device to provide) user-perceptible signals, such as exercise instructions or messages. For example, the display 204 and one or more loudspeakers of the audio system 206 may provide such user-perceptible signals. That is to say, the user device 108 may comprise one or more of visual output means, audio output means, vibrating means, or other means for providing user-perceptible signals in the form of sounds, vibration, animated graphics, etc.

For example, the display 204 of the user device 108 may show instructions and/or information to the patient 110 about the digital physical therapy program, such as predetermined movements that are to be performed by the patient 110, a list or representation of the body members that should have a tracker arranged thereon for a given exercise or motion tracking procedure, or results of the exercises performed by the patient 110. The user device 108 may thus provide a user interface to present instructions and/or information to the user and/or to receive inputs from the user. Any of these data items can be transmitted to and/or received from another electronic device thanks to communicative couplings between the user device 118, the digital therapy platform 102, and the user device 108 (e.g., over the network 106 of FIG. 1). For example, the physical therapist 120 is able to receive the feedback at the user device 118 in a hospital (or other facility, such as an outpatient clinic, retirement home, or elderly care facility) so as to monitor the evolution or progress of the patient 110.

In some examples, one or more of the trackers 208, 210 may include a vital sign sensor. Examples of vital sign sensors include a respiration rate sensor, a body temperature sensor, a pulse rate sensor, or a combination of two or more thereof. In some examples, one or more of the trackers 208, 210, or the user device 108, also captures audio feedback via one or more audio sensors such that the audio feedback can be processed by the user device 108 or at the digital therapy platform 102 (e.g., to assist in determining the ease or difficulty experienced by the patient 110 in performing the exercises).

The physical therapist 120 may manage, edit, or track the digital physical therapy programs of various patients on the user device 118. For example, based on sensor measurements and user-reported feedback received with respect to the patient 110, the physical therapist 120 is able to adjust the digital physical therapy program by changing the difficulty of the movements or exercises, changing the number of repetitions thereof, prescribing new movements, and so forth. The patient 110 may also be provided with educational content (e.g., tailored educational content) and/or CBT via the digital therapy application.

The digital therapy platform 102 may provide for bidirectional communication with patients, for example, through a secure chat functionality available when the digital therapy application is installed on the user device 118 and the user device 108. This may enable, for example, virtual consultations between patients and physical therapists. The user device 118 also includes, or is connected to, a camera 212, for example, to facilitate such communications. As discussed with reference to the user device 108, the user device 118 also includes a display 214, at least one processor, at least one memory, and a communication module (not shown) for communicating with the digital therapy platform 102 and one or more other devices.

A therapy workflow 216 may be provided to the physical therapist 120 via a user interface presented on the display 214. For example, after authenticating into the digital therapy platform 102 (e.g., logging into the digital therapy application), the physical therapist 120 can access a therapy workflow 216 for their assigned patients (e.g., the patient 110) or for each assigned patient. The therapy workflow 216 may form part of an interface provided by a patient management system of the digital therapy platform 102. The therapy workflow 216 may visualize baseline information, patient data over time, including, for example, measured range of motion (e.g., using the trackers 208, 210 or computer vision techniques), self-reported pain ratings (e.g., a reported pain level after each session), utilization data, and/or fatigue levels. The therapy workflow 216 may provide predicted risk alerts (as described in greater detail below), next steps, tasks, and/or timeline views of exercise activity to assist the physical therapist 120. The therapy workflow 216 may also enable the physical therapist 120 to prescribe physical therapy interventions by selecting exercise regimens and scheduling follow-ups. In some examples, the therapy workflow 216 is dynamically and automatically adjusted or updated to reflect the current state of the patient 110 based on the latest measurements and predictions.

In some examples, the digital therapy platform 102 includes a patient management system and a patient messaging system. In some examples, through the combination of the patient management system and the patient messaging system, the digital therapy platform 102 provides end-to-end, AI-powered digital therapy.

The patient management system may be configured to process patient data and detect patient events. For example, when a patient event (e.g., completion of a therapy session, arrival of a new chat message, or a lack of patient engagement for a predetermined number of days) occurs, the patient management system automatically recommends an action through analysis of patient data (e.g., recent changes in patient data). The action may be recommended via a patient management user interface, such as via the therapy workflow 216, in some examples.

The patient management system may follow clinical guidelines to recommend an action to a (human) therapist. For example, the patient management system may recommend to the therapist to adjust the digital therapy program to change the content of upcoming sessions, send a message to the patient, or intervene in some other way. The (human) therapist can then act efficiently, more quickly, and with greater context, understanding why an action is being recommended.

In some examples, the patient management system analyzes baseline patient data (e.g., individual characteristics, clinical conditions, patient needs, and/or goals) and sets an initial prescription (e.g., a starting protocol for a digital therapy program). The initial prescription can be assigned to the patient profile of the patient automatically or subject to therapist review/approval. The patient management system handles data from various data sources in order to generate the initial prescription. The data may include structured data and unstructured data.

The patient management system can automatically monitor patient progress over time (e.g., by checking sensor data, patient feedback from therapy sessions, and therapist notes) and introduce tailored prescription adjustments. In some examples, the patient management system generates recommended modifications for therapist review/approval. For example, the patient management system can automatically detect or predict that the patient is struggling with an exercise and recommend removal of that exercise from future sessions. As another example, the patient management system can automatically detect or predict that the patient is performing well and recommend increasing a difficulty level of future sessions.

The patient management system can also handle patient communications, or parts thereof. For example, the patient management system may analyze patient data and program context and generate recommended messages for transmission to the patient. The recommended messages may be subject to therapist review/approval. Messages may be delivered to the patient proactively (e.g., in response to detecting that the patient is struggling with an exercise) or in response to receiving a message from the patient.

In some examples, the patient management system leverages rules-based techniques and/or AI-driven techniques to perform its functions. The patient management system may utilize generative machine learning models, such as LLMs. In some examples, an LLM is fine-tuned on historic data of the digital therapy platform 102 (e.g., historic digital therapy programs, patient outcomes, and therapist-patient interactions) to improve the ability of the LLM to generate effective adjustments or recommendations.

The patient management system thus, in some examples, provides digital therapy program management as well as patient support to improve the efficiency of the digital therapy platform 102. The patient messaging system can supplement or complement the patient management system by handling at least some patient communications, as described in greater detail below.

In some examples, the patient messaging system is responsible for in-session interactions with the patient. For example, the patient messaging system may generate personalized messages that are delivered to the patient at certain points in time, and may also automatically respond to patient queries during a session. The patient messaging system can also, in some cases, be responsible for delivering messages originating from the patient management system. For example, where the patient management system recommends sending a motivational message to the patient between sessions (e.g., in response to detecting a patient event resulting from the patient not attending any sessions for a predetermined number of days) and the recommendation is approved by the therapist, the motivational message can be transferred to the patient messaging system for delivery or surfacing.

Where the patient messaging system interacts with the patient in real time during a therapy session, the patient messaging system may generate and transmit messages rapidly, without requiring user input, and thus simulating the role of a human therapist who is working with and/or encouraging the patient in real time.

Merely as an example, in the context of digital physical therapy, functions may be performed by three entities: a human clinician/therapist, an "AI clinician," and an "AI physical therapist." The patient management system may perform functions of the "AI clinician," processing patient data and providing personalized recommendations for review by the human clinician/therapist. The patient messaging system may perform functions of the "AI physical therapist," handling patient interactions (including real-time exercise instructions and real-time personalized messages) during therapy sessions. In other words, the digital therapy platform 102 can include a first AI assistant that manages the digital therapy program of the patient and a second AI assistant that conducts the sessions with the patient. These AI assistants may automatically communicate with each other. In this way, the human clinician/therapist can operate significantly more efficiently.

Figure 3:
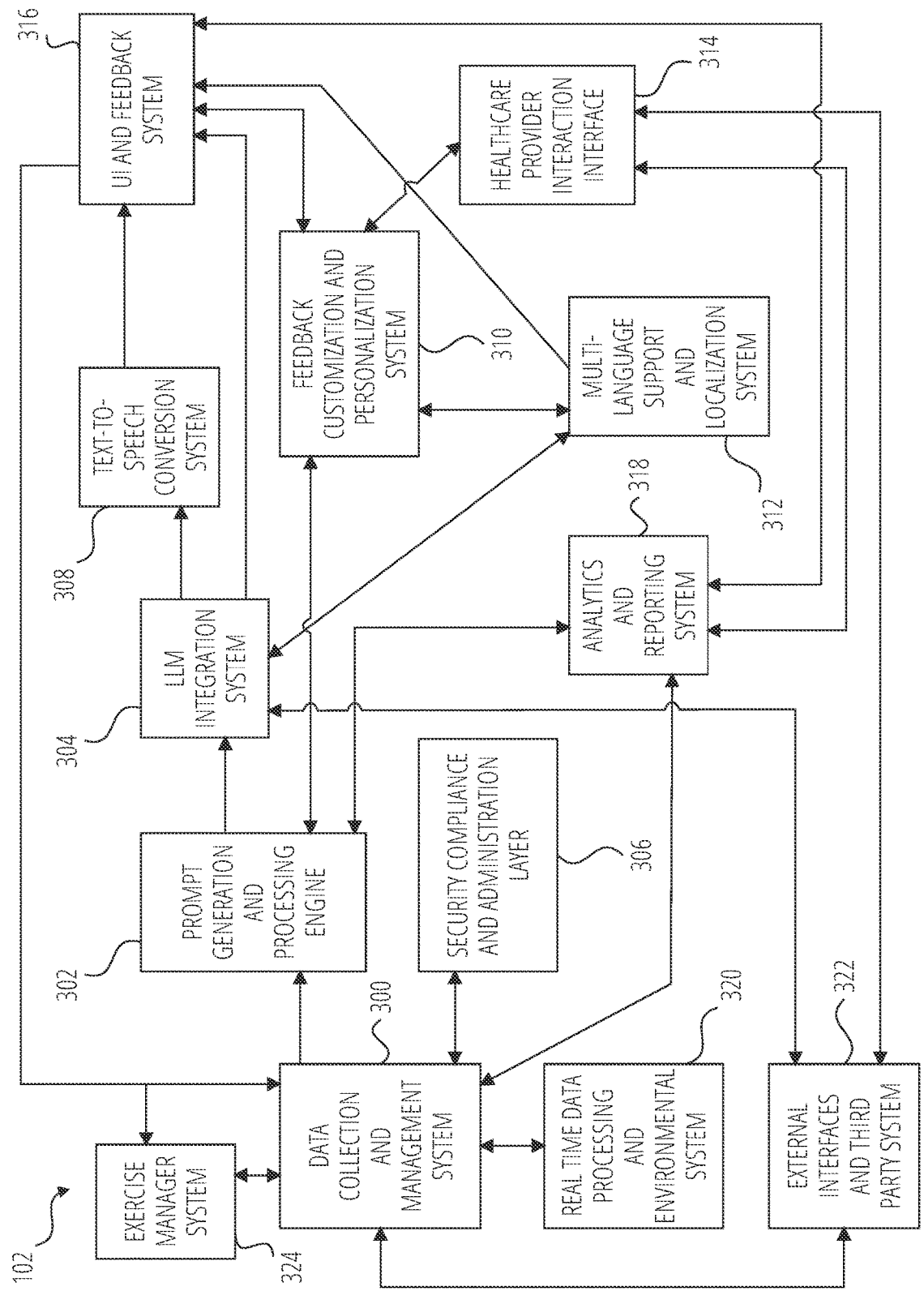
FIG. 3 is a flowchart depicting an architecture for a digital therapy platform, according to some examples, demonstrating the interconnectedness of various system components.

Digital Therapy Platform Architecture (FIG. 3)

Referring now to FIG. 3, a schematic diagram is shown of certain components of the digital therapy platform 102 of FIG. 1, according to some examples. FIG. 3 illustrates the interconnection and cooperation of various systems and subsystems to facilitate the generation and delivery of personalized messages to patients undergoing digital therapy. As mentioned elsewhere, in a server-client architecture, one or more components of the digital therapy platform 102 may be provided server-side, client-side, or both server-side and client-side. The systems and/or components shown in FIG. 3 (or a subset thereof) may provide a patient messaging system. As mentioned, in some examples, the patient messaging system works with a patient management system to provide an end-to-end digital therapy solution.

A data collection and management system 300 serves as a repository for patient-related data. The data collection and management system 300 may communicate with or include a multitude of sensors and data acquisition devices (e.g., the camera 202, audio system 206, tracker 208, and tracker 210) that capture real-time performance metrics during therapy sessions. The data collection and management system 300 may also store or access other patient data, such as data collected in an onboarding questionnaire that includes demographic, clinical, prescription, behavioral, and/or social data. The data collection and management system 300 is responsible for the aggregation, normalization, and storage of both real-time and historical patient data. It ensures that data integrity is maintained and that the data is readily accessible for processing by other systems within the platform. The data collection and management system 300 may communicate with an exercise manager system 324 to obtain real-time information regarding, for example, exercises or repetitions being performed by a patient during a session.

A prompt generation and processing engine 302 operates as a hub within the digital therapy platform 102, interfacing directly with the data collection and management system 300. The data collection and management system 300 is an assembly of hardware and software components designed to gather and organize a wide array of patient-specific data during therapy sessions. This data may encompass a variety of metrics, such as range of motion, exercise completion rates, and the accuracy of movements, all of which are helpful for assessing the patient's adherence to the prescribed therapy regimen and their overall progress.

Upon receiving this processed data, the prompt generation and processing engine 302 employs algorithms to interpret and analyze the incoming information. These algorithms are part of a larger, intelligent framework that is capable of understanding the nuances of physical therapy and the unique requirements of each patient. Functionality of the prompt generation and processing engine 302 implements the dynamic generation of structured prompts, which are crafted to be specific to the individual patient's current therapy session.

The prompt generation and processing engine 302 may include a rules-based logic processor. This processor includes a set of predefined rules, developed in close collaboration with medical professionals to ensure clinical accuracy and relevance. The rules are designed to evaluate the incoming data and prioritize it based on a hierarchy of clinical significance. For instance, if a patient demonstrates a marked improvement in their range of motion, this positive development would be flagged as a high-priority data point and subsequently highlighted in the generated prompts.

The prioritization process is not merely a binary operation but a decision-making protocol that takes into account the multifaceted nature of therapy data. It may consider factors such as the patient's historical performance, the specific goals of the current therapy session, and pertinent medical notes that may influence the direction of the therapy. By doing so, the prompt generation and processing engine 302 ensures that impactful information is distilled and presented in the prompts.

These prompts serve as the input for subsequent systems in the digital therapy platform, particularly an LLM integration system 304. The prompts are structured in a manner that facilitates an LLM's understanding and generation of personalized messages, which are then conveyed to the patient to encourage engagement and adherence to the therapy program. Through data collection, processing, and prompt generation, the digital therapy platform 102 may achieve a high level of personalization and clinical efficacy.

A security compliance and administration layer 306 provides a framework to protect sensitive patient data and ensure compliance with relevant healthcare regulations. The security compliance and administration layer 306 includes encryption protocols, secure data transmission mechanisms, and compliance monitoring tools. It also offers administrative functionalities, such as user access control and system configuration management, to maintain the integrity and security of the digital therapy platform 102.

The LLM integration system 304 is an interface that serves as the conduit between the prompt generation and processing engine 302 and the relevant LLM (e.g., LLM 140 of FIG. 1). The LLM integration system 304 thus facilitates communications with one or more AI models that are capable of natural language understanding and generation. It will be appreciated that the LLM integration system 304 is a non-limiting example and that the prompt generation and processing engine 302 may interface with other systems to communicate with other types of AI models, such as other generative AI models.

Upon receiving the structured prompts, which are composed of semantically rich and contextually relevant data points, the LLM integration system 304 initiates a secure and efficient data exchange protocol with one or more LLM. This protocol is designed to transmit the prompts to an LLM in a format that is optimized for AI processing, for example, leveraging both natural language and JavaScript Object Notation (JSON) (or similar structured data formats) to encapsulate the nuances of the therapy session data.

In some examples, the LLM 140, residing, for example, either on local servers or accessed via cloud-based services, receives the prompts through a dedicated API endpoint. The LLM140 then employs pre-trained neural networks, which have been fine-tuned on corpuses of language data, to interpret the prompts and generate responses. These responses are crafted to be not only syntactically and grammatically correct but also empathetic and motivational, reflecting the therapeutic intent of the prompts.

The responses of the LLM 140 are then transmitted back to the LLM integration system 304, which may perform an initial validation check to ensure the integrity and appropriateness of the messages. This validation process may involve checking for compliance with predefined therapy guidelines and ensuring that the tone and content of the messages are suitable for patient consumption.

Once validated, the personalized messages are queued for conversion into audio format by a text-to-speech conversion system 308. The text-to-speech conversion system 308 is equipped with speech synthesis algorithms that are capable of transforming text into lifelike speech. The conversion process may take into account various factors such as intonation, cadence, and pronunciation to produce audio feedback that is as natural-sounding as possible.

The text-to-speech conversion system 308 is designed to support a range of voices and languages, allowing for customization according to patient preferences. The text-to-speech conversion system 308 also includes real-time processing capabilities, ensuring that the conversion from text to speech occurs with minimal latency. This maintains the flow of the therapy session and provides reinforcement or correction to the patient.

The resulting audio feedback is then streamed to the patient's interface. For example, the audio feedback can be delivered through speakers, headphones, or other audio output devices associated with the audio system 206 of the user device 108 of the patient 110 of FIG. 1 and FIG. 2. The delivery mechanism may be designed to be flexible, accommodating various patient environments, whether it be a home setting, a rehabilitation facility, or a mobile application.

In some examples, the LLM integration system 304 and the text-to-speech conversion system 308 thus work in tandem to provide a seamless and interactive experience for patients. They leverage AI and speech synthesis technologies to deliver personalized, real-time feedback that enhances the efficacy of digital therapy sessions.

The prompt generation and processing engine 302 may be responsible for tailoring the feedback to meet the individual preferences and needs of each patient. In some examples, a feedback customization and personalization system 310 operates with the prompt generation and processing engine 302 to use patient profiles and adaptive algorithms to customize the feedback based on language preferences, feedback modality, and/or other personalization parameters.

In some examples, to cater to a diverse patient population, a multi-language support and localization system 312 provides translation and localization services. The multi-language support and localization system 312 ensures that the platform is accessible to patients in their preferred language and that the feedback is culturally appropriate and regionally customized.

A healthcare provider interaction interface 314 facilitates the interaction between healthcare providers and the digital therapy platform 102. In some examples, providers can use the healthcare provider interaction interface 314 to review generated feedback, make adjustments, and provide clinical input to enhance the therapeutic experience for the patient. A healthcare provider may, for example, be a physical therapist assigned to a particular patient (e.g., the physical therapist 120 of FIG. 1 and FIG. 2).

A UI and feedback system 316 constitutes the interface layer of the digital therapy platform 102, directly interacting with the user device of the patient. This system is designed to present personalized motivational messages in an accessible and engaging way. User interfaces are rendered on output devices, such as the user device 108 of FIG. 1 and FIG. 2. However, it is noted that output devices which may range from conventional computer screens to mobile devices, wearable technology, or specialized medical equipment displays, depending on the patient's needs and the therapy environment.

In some examples, the UI and feedback system 316 is further engineered to manage the delivery of feedback in multiple formats. For example, the UI and feedback system 316 transitions between text and audio modalities, providing patients with the flexibility to receive feedback in the format that best suits their current activity or personal preference. For instance, a patient engaged in a physical therapy exercise may find audio feedback more convenient, as it allows them to maintain focus on their movements without the need to divert their gaze to a screen.

In some examples, the user interface presented at a user device prioritizes ease of use and minimizes cognitive load. For example, the user interface employs navigation schemes, clear visual cues, and responsive design principles to ensure that patients of all ages and technological proficiencies can interact with the digital therapy platform 102 without difficulty. The user interface may also be customizable, allowing for adjustments in font size, color schemes, and other accessibility settings to accommodate patients with visual or auditory impairments.

In some examples, feedback delivery is orchestrated by a feedback management engine within the UI and feedback system 316. This engine is responsible for queuing feedback messages from the feedback customization and personalization system 310, scheduling their presentation, and ensuring that they are delivered in synchronization with the flow of a therapy session. The UI and feedback system 316 may take into account the real-time context of the session, delivering motivational messages at the most impactful moments, such as immediately following an exercise or at the conclusion of a session.

The feedback management engine of the UI and feedback system 316 may also incorporate logic to handle patient responses or interactions with the feedback. For example, if a patient acknowledges a message or asks a follow-up question, the UI and feedback system 316 is equipped to capture this input and, if necessary, operate with the feedback customization and personalization system 310 to trigger an additional response or action via the prompt generation and processing engine 302, such as providing further clarification via the LLM (facilitated by the LLM integration system 304) or alerting a healthcare provider. In some examples, patient messages that are received by the UI and feedback system 316 are provided to the data collection and management system 300 for storage or processing. The patient messages received by the UI and feedback system 316 may also be transmitted to the exercise manager system 324. For example, the patient may provide an instruction, such as a verbal instruction to skip a particular exercise, causing the exercise manager system 324 to update a current exercise session accordingly, in real time.

The UI and feedback system 316 serves as a primary touchpoint for patients. It is designed with a deep understanding of the therapeutic context and patient needs, ensuring that the delivery of personalized motivational messages is not only timely and effective but also contributes positively to the patient's therapy experience.

As mentioned, in some examples, a patient management system can also generate messages to be delivered to the patient. For example, the patient management system may analyze a patient's performance trajectory and generate a recommendation to a therapist to transmit, to the patient, a message. If approved, this message is then provided to the UI and feedback system 316 to present to the patient. In such cases, the personalized message can be presented between sessions (e.g., not necessarily in-session). In this way, a patient messaging system provided using components of FIG. 3 may operate with a patient management system to improve the patient's holistic therapy experience.

An analytics and reporting system 318 processes data collected during therapy sessions, transforming this data into actionable insights that can significantly impact the therapeutic process. In some examples, the analytics and reporting system 318 employs data analytics techniques to process real-time and historical patient data, identifying performance indicators, trends, and patterns. It may generate reports and visualizations that succinctly summarize the patient's progress, adherence to the therapy regimen, and response to treatment. These reports are not only informative but are also designed to be intuitive, allowing for quick interpretation and decision-making by both patients and healthcare providers.

To facilitate a collaborative approach to patient care, the analytics and reporting system 318 may provide input to the healthcare provider interaction interface 314. To this end, the healthcare provider interaction interface 314 acts as a gateway for healthcare providers to access the analytics reports and visualizations, enabling them to monitor their patients' progress, adjust treatment plans, and provide personalized guidance based on empirical data. In some examples, the healthcare provider interaction interface 314 is designed to be user-friendly, ensuring that providers can easily navigate through the analytics information and extract the insights they need to optimize patient care. In some examples, the healthcare provider interaction interface 314 acts as a gateway between the patient management system accessed by a therapist and the patient messaging system provided by components shown in FIG. 3.

The analytics and reporting system 318 may also be communicatively coupled to the UI and feedback system 316. This coupling allows the analytics and reporting system 318 to present various analytics information directly to the patients via the UI and feedback system 316. Patients can thus engage with their own therapy data, gaining a better understanding of their progress, challenges, and achievements. This level of transparency and patient involvement is helpful for fostering a sense of ownership and empowerment in the therapy process.

The user interface, as part of the UI and feedback system 316, presents analytics information in a manner that is accessible and meaningful to patients. It may include features such as progress trackers, graphical representations of therapy milestones, and personalized feedback based on analytics findings. By presenting this information in a clear and engaging format, the UI and feedback system 316 encourages patients to take an active role in their therapy, leading to increased motivation and adherence.

In some examples, the analytics and reporting system 318 thus provides both healthcare providers and patients with the tools they need to understand therapy outcomes and make informed decisions. Its integration with the healthcare provider interaction interface 314 and the UI and feedback system 316 ensures that the insights derived from therapy data are effectively communicated and utilized to enhance the overall therapy experience.

As further shown in FIG. 3, a real time data processing and environmental system 320 processes live data inputs and integrates environmental factors that may impact the therapy session. In some examples, the real time data processing and environmental system 320 ensures that the feedback remains contextually relevant and that any changes in the therapy environment are accounted for in real-time. The real time data processing and environmental system 320 may be configured for the analysis of data collected from sensors, wearables, or computer vision systems that monitor the patient's movements and physiological responses. This data includes, but is not limited to, joint angles, muscle activation levels, movement velocity, and exercise completion rates. By processing this data in real-time, the real time data processing and environmental system 320 can enable the digital therapy platform 102 to provide real-time feedback to the patient, allowing for immediate adjustments to be made to their exercise form or intensity, which may be crucial for preventing injury and ensuring the exercises are performed correctly. The real time data processing and environmental system 320 may also be notified of any real-time changes in patient exercise, e.g., via the exercise manager system 324 that communicates such data to the data collection and management system 300.

In some examples, in addition to performance data, an environmental data component of the real time data processing and environmental system 320 captures and integrates environmental factors that may affect the therapy session. These factors could include the room temperature, lighting conditions, noise levels, and even the time of day. For example, if the room is too hot, it may affect the patient's endurance and performance; if the lighting is poor, it may impact the patient's ability to perform exercises with proper form; and if there is significant background noise, it may distract the patient and reduce the effectiveness of audio feedback.

In some examples, the real time data processing and environmental system 320 is equipped with algorithms that can adapt the feedback based on these environmental factors. For instance, if the real time data processing and environmental system 320 detects that the patient is performing exercises at a time when they typically have low energy levels, the feedback of the feedback customization and personalization system 310 can be adjusted to cause the prompt generation and processing engine 302 to request messages that are more encouraging and supportive to help boost the patient's motivation.

Furthermore, the real time data processing and environmental system 320 is designed to be dynamic, with the ability to learn from each session and improve its understanding of how environmental factors impact individual patients. This learning capability allows the digital therapy platform 102 to provide increasingly personalized feedback that accounts for the unique preferences and sensitivities of each patient.

By ensuring that the feedback remains contextually relevant and accounts for changes in the therapy environment in real-time, the real time data processing and environmental system 320 plays a role in maintaining the efficacy and personalization of the digital therapy sessions. The real time data processing and environmental system 320 may thus assist in providing an adaptive, responsive, and patient-centered therapeutic experience.

An external interfaces and third party system 322 is a component of the digital therapy platform 102, serving as a gateway for integrating external data sources, healthcare systems, third-party services, or combinations thereof. The external interfaces and third party system 322 may be engineered to facilitate interoperability between the digital therapy platform 102 and various external entities, thereby enriching the capabilities of the digital therapy platform 102 and extending its functionality beyond its core offerings.

For example, through the external interfaces and third party system 322, the digital therapy platform 102 can connect to a multitude of external data sources, such as electronic health records, medical databases, and patient health applications. By accessing these sources, the digital therapy platform 102 can import patient data, including medical history, treatment plans, and biometric information, which can be used to enhance the personalization and accuracy of the therapy sessions.

In addition to data sources, the external interfaces and third party system 322 may enable the digital therapy platform 102 to interface with healthcare systems, such as hospital information systems and practice management software. This integration may allow for a two-way exchange of information, where therapy data generated by the platform can be shared with healthcare providers, and updates from the providers can be reflected in the digital therapy platform 102.

Third-party services may include analytics tools, content providers, or specialized medical applications that offer additional features such as advanced exercise libraries, nutritional guidance, or mental health support. By interfacing with these services, the digital therapy platform 102 may offer a more comprehensive therapy experience that addresses the multifaceted needs of patients.

Figure 4:
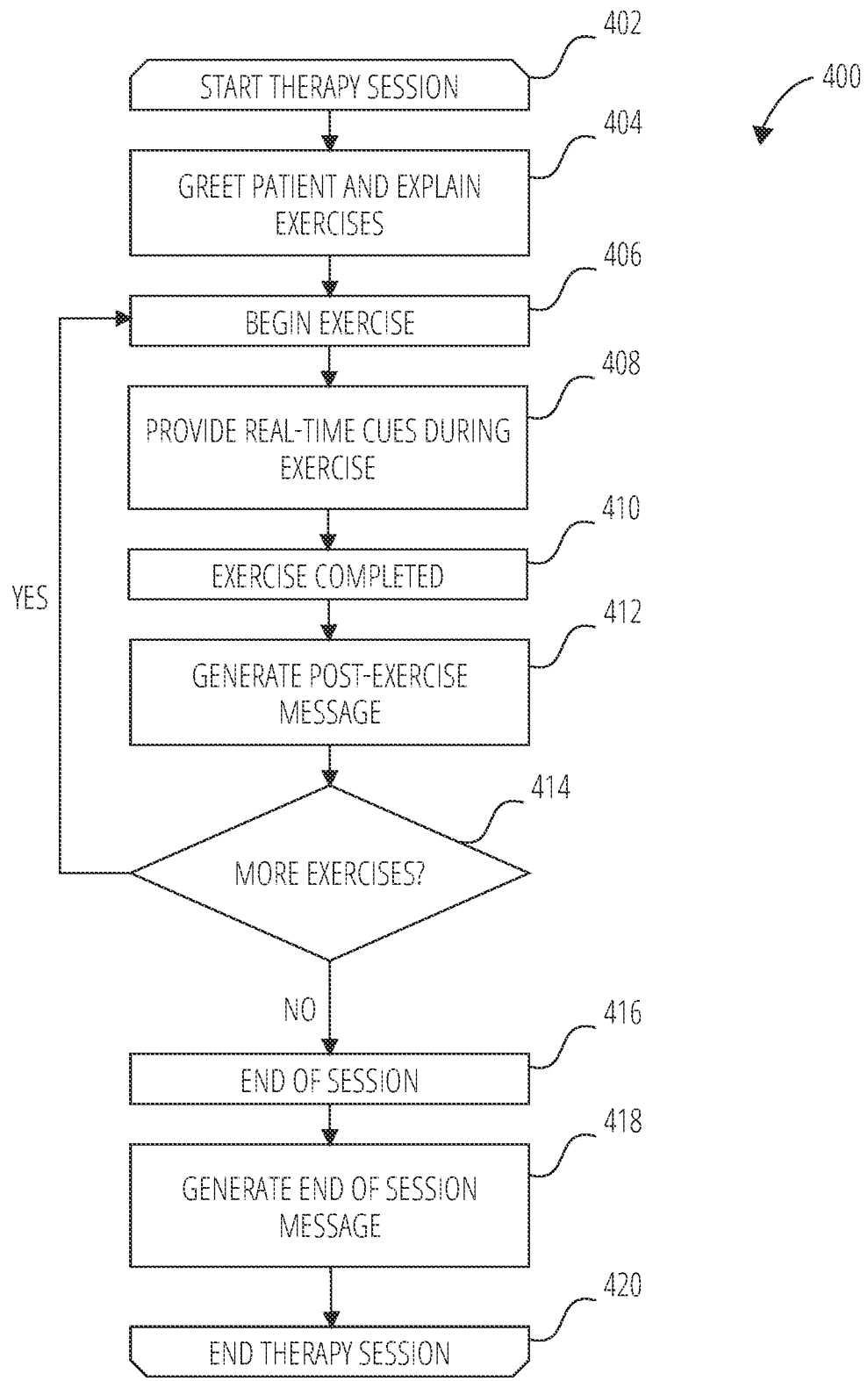
FIG. 4 is a flowchart outlining operations in a therapy session in a digital therapy platform, according to some examples.

Digital Therapy Session (FIG. 4)

FIG. 4 illustrates a method 400 to conduct a digital therapy session, according to some examples. Although the example method 400 depicts a particular sequence of operations, the sequence may be altered without departing from the scope of the present disclosure. For example, some of the operations depicted may be performed in parallel or in a different sequence that does not materially affect the function of the method 400. In other examples, different components of an example device or system that implements the method 400 may perform functions at substantially the same time or in a specific sequence.

By way of introduction, the method 400, as may be performed by the digital therapy platform 102, seeks to enhance the patient's experience by providing timely and contextually relevant AI-generated messages that serve as touchpoints throughout a therapy session. These messages may be delivered at three junctures: the beginning of the session, after the completion of each exercise, and at the session's conclusion. However, it will be appreciated that, in other examples, messages may be delivered at different times or in different sequences.

Referring specifically to the method 400, at the onset of the therapy session, the digital therapy platform 102 generates a welcoming message that is personalized to the patient's profile, taking into account factors such as their progress in the therapy program and the specific time of day. This initial interaction sets a positive and encouraging tone, aiming to motivate the patient and prepare them mentally for the session ahead.

The therapy session may comprise performance of a plurality of exercises. Following each exercise, the digital therapy platform 102 conducts an analysis of the patient's performance using algorithms that assess a variety of metrics, such as range of motion, pelvic area movements or forces, and/or the accuracy of movements. Based on this analysis, the digital therapy platform 102 crafts a post-exercise message that provides personalized feedback. This feedback is not only informative, giving the patient insight into their performance, but also, where relevant, motivational, highlighting their achievements and areas of improvement in a manner that encourages perseverance and dedication.

As the session draws to a close, the digital therapy platform 102 synthesizes data from the entire session to generate a concluding message. This message serves as a summary of the patient's performance throughout the session, reinforcing positive behaviors and accomplishments while also setting goals and expectations for future sessions. In some examples, it is designed to leave the patient with a sense of achievement and a clear understanding of their progress on their therapeutic journey.

The digital therapy platform 102, through its intelligent use of AI messaging, creates a supportive environment that mirrors the interaction a patient would have with a human therapist. By providing real-time, adaptive feedback, the system ensures that each therapy session is a personalized and engaging experience, fostering an atmosphere conducive to recovery and rehabilitation.

Referring now specifically to the flowchart in FIG. 4, according to some examples, the method 400 includes starting a therapy session at opening loop element 402. The digital therapy platform 102 initiates a new session when the patient logs in, opts to start, or when a scheduled session time arrives. The digital therapy platform 102 loads the patient's profile (e.g., as part of the digital therapy application described above), including scheduled exercises and historical data from previous sessions.

At operation 404, the digital therapy platform 102 engages in an initial patient interaction and instructional phase of the therapy session. As the session commences, the digital therapy platform 102 activates a personalized communication protocol, generating a welcoming message that is tailored to the patient's identity and current context. This message is not merely a generic greeting; it is a thoughtful composition that incorporates the patient's name, acknowledging their presence and participation. Additionally, the digital therapy platform 102 intelligently considers contextual factors such as the time of day—for example offering a bright "Good morning" or a calming "Good evening"—and the patient's journey within the therapy program, recognizing milestones or encouraging continued progress.

Following the personalized greeting, the digital therapy platform 102 transitions to an educational mode, where it provides a detailed and understandable explanation of the exercises that are slated for the session. This instructional content is designed to be clear and succinct, ensuring that the patient comprehensively understands the activities they are about to undertake. To cater to diverse learning preferences and accessibility needs, the digital therapy platform 102 employs a variety of instructional mediums. Visual learners may benefit from illustrative aids such as diagrams or animated sequences that demonstrate the exercises, while auditory learners may prefer spoken instructions delivered through the text-to-speech conversion system 308 and the UI and feedback system 316. For patients 110 who favor reading or require written instructions to supplement their understanding, the digital therapy platform 102 can generate descriptive text. The choice of instructional medium is determined by the patient's pre-set preferences and the technological capabilities of the digital therapy platform 102, ensuring that each patient receives information in the most effective and comfortable format for them.

The method 400 initiates the exercise regimen at operation 406. This stage marks the transition from preparatory activities to the active engagement of the patient in their prescribed therapeutic exercises. As the patient embarks on the first exercise, the digital therapy platform 102 serves as an interactive guide, providing real-time instructions to ensure that the patient performs each movement with precision and care.

The digital therapy platform 102, equipped with monitoring capabilities, digitally captures data regarding the patient's movements (and, in some cases, other data, such as vital signs). Utilizing an array of sensors or computer vision technology, the digital therapy platform 102 captures a detailed account of the patient's kinematics, providing a comprehensive analysis of each motion. This technology is not merely for observation; it is an integral part of a feedback loop that ensures the patient's adherence to the correct form and technique.

As the patient progresses through the exercise, the digital therapy platform 102 analyzes each movement for accuracy and consistency. Should the patient deviate from the prescribed form, the digital therapy platform 102 may intervene. The digital therapy platform 102 may do so by offering corrective cues, which are designed to be intuitive and easily actionable, allowing the patient to adjust their movements in real-time. This immediate or real-time feedback is helpful for preventing potential injuries and ensuring that the therapeutic benefits of the exercise are fully realized.

Specifically, in some examples, the method 400 includes providing real-time, personalized cues during exercise at operation 408. As the patient performs the exercise, the digital therapy platform 102 analyzes the movement or other data in real-time. If deviations from the correct form are detected, the digital therapy platform 102 provides cues tailored to the patient's immediate needs to correct their posture or movement. These personalized cues can facilitate an interactive conversation between the "digital therapist" (e.g., "AI physical therapist") provided by the digital therapy platform 102 and the patient, enhancing the adaptability of the session to the patient's capabilities and responses. For example, the digital therapist might observe and comment, "You're struggling a bit with the upward part of the movement as you are losing your balance." If the patient acknowledges the difficulty, responding with "Indeed, but I don't seem to be able to do it!" the digital therapist can then offer actionable advice, such as "Just focus on keeping your knees in place and rise slowly." The communication is designed to be actionable, providing the patient with specific, real-time guidance that can be immediately implemented to improve performance and ensure safety. Additionally, the system is equipped to handle requests from the patient, such as asking the digital therapist to skip an exercise due to pain. In such cases, the digital therapist can respond with understanding and adapt the session accordingly, either by suggesting an alternative exercise or by providing reassurance and instructions for managing discomfort. As mentioned above, for example, the exercise manager system 324 may be integrated with other components of the digital therapy platform 102 to allow for real-time adjustments to exercise sessions. This level of personalized and actionable interaction aims to create a supportive and responsive digital therapy environment.

According to some examples, the method 400 includes automatically determining that an exercise is completed at operation 410. Once the patient completes the exercise, the system processes the performance data to determine the quality of the exercise execution, such as the range of motion achieved and the accuracy of movements. For example, the digital therapy platform 102 uses the described sensor integration that enables it to monitor and analyze the patient's movements in real time. When the patient performs an exercise, the digital therapy platform 102 utilizes motion tracking technology, such as the sensors described above and/or or computer vision, to capture detailed data on the patient's movements. This data may include the speed, acceleration, and trajectory of limbs, as well as the overall posture and alignment of the body during the exercise. Upon the completion of an exercise, the system automatically detects this event using criteria such as the cessation of movement, the achievement of a target range of motion, or the completion of the expected number of repetitions.

According to some examples, the method 400 includes generating a post-exercise message at operation 412. For example, the digital therapy platform 102 may use performance data to generate a post-exercise message. This message includes personalized feedback on the patient's performance, highlighting achievements like improved range of motion or a high percentage of correct movements. The message is crafted to be motivational and encouraging, using positive reinforcement techniques.

At decision operation 414, the digital therapy platform 102 determines whether the therapy session includes further exercises scheduled for the physical therapy session. If more exercises are planned, the digital therapy platform 102 proceeds to guide the patient to the next exercise at operation 406. If not, the digital therapy platform 102 transitions to the end-of-session phase.

Following a determination, at decision operation 414, that no further exercises are scheduled for the physical therapy session, the digital therapy platform 102 ends the session at operation 416. At the culmination of the therapy session, the digital therapy platform 102 engages in a process of data compilation and synthesis. This process is not merely an aggregation of statistics but a strategic assembly of insights drawn from the patient's exertions during the session.

The digital therapy platform 102 evaluates the patient's performance, distilling the essence of their efforts into a coherent end-of-session message which is generated at operation 418. This message serves as a comprehensive overview, providing the patient with a clear picture of their performance, including progress made towards their therapy goals. It is a reflection of the patient's journey through the session, capturing moments of strength, instances of improvement, and areas that may require further attention. The ability of the digital therapy platform 102 to personalize this end of session message uses the analytics technologies—described in further technical detail herein—of the patient's therapeutic needs.

Moreover, the end-of-session message includes motivational elements, designed to motivate the patient to persist with their therapy regimen. It is a blend of commendation and encouragement, acknowledging the patient's hard work and dedication. The message may highlight specific accomplishments, such as achieving a new personal best in range of motion or maintaining a consistent pattern of correct movements, which are significant milestones in the patient's therapy journey.

In some examples, the message also serves as a bridge to future sessions, providing the patient with a sense of continuity and progression. It reinforces the patient's overall trajectory of improvement, celebrating the cumulative successes while also setting the stage for subsequent therapy sessions. This forward-looking perspective helps maintain the patient's focus and motivation, ensuring that they remain engaged and committed to their long-term therapy goals.

Thus, in some examples, the end-of-session message crafted by the digital therapy platform 102 is a multifaceted communication tool that encapsulates the patient's session performance, fosters a positive outlook on their therapy journey, and encourages steadfast participation in their prescribed rehabilitation program.

According to some examples, the method 400 includes ending the therapy session at closing loop element 420. The digital therapy platform 102 officially ends the session, logs the session data (e.g., using the data collection and management system 300) for future reference, and may schedule the next session based on the patient's therapy plan. The patient may then log out or be logged out (e.g., of a digital therapy application as described above), or the system shuts down until the next scheduled session.

Figure 5:
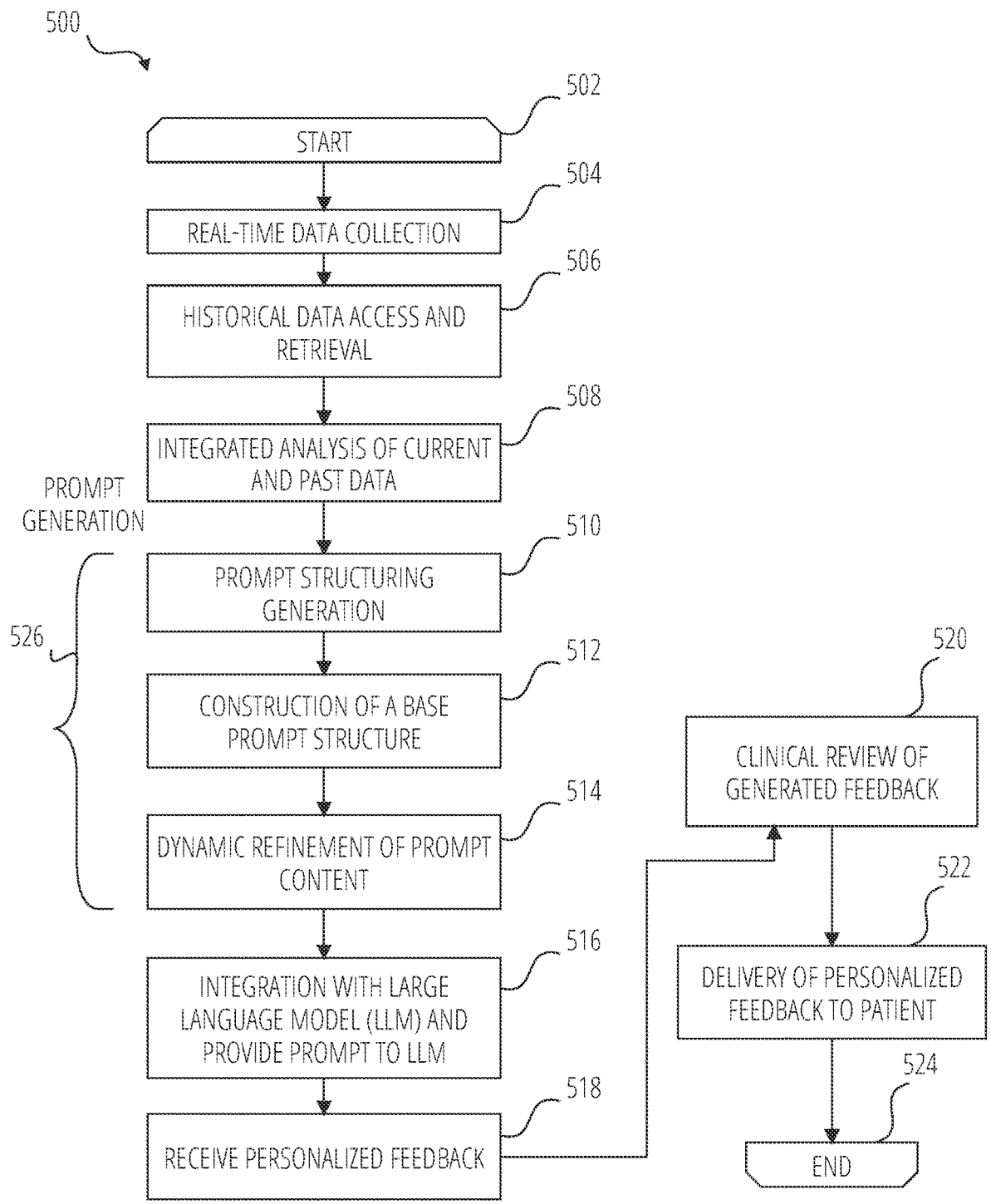
FIG. 5 is a flowchart outlining a process for generating personalized interactions in a digital therapy platform, according to some examples.

Automatically Generating Personalized Interactions (FIG. 5)

FIG. 5 is a flowchart illustrating a method 500, according to some examples, to automatically generate personalized interactions for a patient. Although the example method 500 depicts a particular sequence of operations, the sequence may be altered without departing from the scope of the present disclosure. For example, some of the operations depicted may be performed in parallel or in a different sequence that does not materially affect the function of the method 500. In other examples, different components of an example device or system that implements the method 500 may perform functions at substantially the same time or in a specific sequence.

The method 500 commences at opening loop element 502.

Real-Time Data Collection (Operation 504)

The method 500 includes real-time (or near real-time) data collection at operation 504.

In some examples, within the architecture of the digital therapy platform 102, as depicted in FIG. 3, the data collection and management system 300 accesses one or multiple sensors and motion tracking devices (e.g., tracker 208, tracker 210, and/or camera 202). These devices may be strategically deployed to capture a broad spectrum of biomechanical data from patients as they perform prescribed therapeutic exercises.

Data collected or analyzed by the sensors or motion tracking devices may include, for example, joint angles, muscle activation, forces due to lengthening or contraction of body parts, and movement velocity (or a subset thereof). Joint angles may be measured to ensure the patient's movements align with the prescribed therapeutic range of motion. This data is used for confirming proper exercise execution and for tracking the patient's progress within their therapy program. Muscle activation may be monitored via electromyography sensors, which provide insights into the patient's muscle engagement during therapy sessions. This information is used for evaluating the effectiveness of the exercises and for detecting any compensatory strategies employed by the patient. Movement velocity is tracked to assess the speed and fluidity with which the patient performs exercises. This metric is indicative of the patient's level of control and the ability to execute exercises with the intended intensity.

The real time data processing and environmental system 320 ensures that the collected data is analyzed, enabling near real-time feedback to the patient. This analysis allows for on-the-fly adjustments to the therapy session, optimizing the therapeutic experience. Concurrently, the real data collection and management system 300 records environmental factors (based on data from the real time data processing and environmental system 320) that may affect the therapy session. These factors may be captured by environmental sensors integrated into the therapy equipment or session environment. For example, equipment settings, such as resistance levels on therapy machines, may be recorded to contextualize the patient's performance data. This information is used to tailor the difficulty of exercises to the patient's current capabilities. Further, a spatial arrangement of therapy equipment and the patient's position within the room may also be documented. This data may be used for understanding how the environment might affect the patient's movements and for ensuring safety during the session.

The data collection and management system 300 receives the information described above, or a subset thereof, from the real time data processing and environmental system 320 and/or the exercise manager system 324 and aggregates this information and incorporates it into the patient's therapy profile. This comprehensive approach to data collection ensures that the feedback provided by the platform is based on the patient's physical performance and considers the therapy environment.

By integrating real-time biomechanical data with environmental factors, the method 500 may provide a detailed understanding of the patient's therapy session. This enables the digital therapy platform 102 to deliver feedback that is precise, personalized, and contextually relevant, enhancing the effectiveness of the therapy sessions.

Historical Data Retrieval (Operation 506)

At operation 506, the data collection and management system 300 of the digital therapy platform 102 engages in the retrieval of historical data. The operation 506 is performed to inform the current therapy session with insights from the patient's past interactions with the digital therapy platform 102.

The data collection and management system 300 may initiate a query to a secure database (e.g., database 130) that is compliant with the Health Insurance Portability and Accountability Act (HIPAA), ensuring that patient data privacy is maintained. This database may serve as a repository for historical data, which may be used for the comprehensive analysis of the patient's therapy journey.

The historical data retrieved may include past performance metrics, which provide a record of the patient's progress over time. These metrics may be helpful for understanding long-term trends in the patient's recovery or improvement and for adjusting current therapy protocols accordingly.

Therapy adherence records may also be accessed, offering a view into the patient's engagement with a therapy program. These records help in identifying patterns of compliance or non-compliance, which can be indicative of the need for modifications to the therapy regimen or additional patient support.

In some examples, previous feedback responses are fetched from the database as well. These responses shed light on how the patient has reacted to past feedback, which can inform the tailoring of new feedback to better resonate with the patient's preferences and motivational triggers. In some examples, the digital therapy platform 102 may, alternatively or additionally, retrieve depersonalized or statistical historical data that does not necessarily include any patient-specific data. For example, the data collection and management system 300 may retrieve data indicative of the average performance of patients in a particular exercise, typical improvement trajectories, or the probability of a patient discontinuing therapy at a particular point in time. In this context, "historical data" or "historical performance data" may thus be specific to a given patient or may be statistical data drawn from a number of patient data points. Accordingly, historical data may be patient-specific historical data related to historical performance of the patient and/or population-based historical data related to historical performance of a group of patients. The population-based data may be obtained through statistical analysis or aggregation of performance data so as to be representative of a group or cohort of patients.

In some examples, the data is structured in a manner that facilitates hierarchical analysis. For example, the data may be stored in JSON format or a similar structured data format, which is adept at maintaining the dependencies and relationships between various data points. This structured approach allows for complex queries that can extract nuanced insights from the patient's therapy history.

In some examples, by maintaining this structured, hierarchical data, the digital therapy platform 102 is equipped to perform in-depth analyses that consider the interplay of various factors affecting the patient's therapy outcomes. The historical context enriches the real-time data collected during current sessions, enabling the platform to provide feedback that is not only personalized but also deeply rooted in the patient's therapy narrative.

Integrated Analysis (Operation 508)

In some examples, the digital therapy platform 102 uses only one of real-time data and historical data to generate a particular message. However, in the method 500, both real-time data and historical data are used. At operation 508 of the method 500, components of the digital therapy platform 102, such as the data collection and management system 300 and the analytics and reporting system 318, undertake an integrated analysis of both current (e.g., real-time or in-session) and historical data. This integration may be used for the generation of a comprehensive feedback loop that informs the therapy process.

Algorithms of the analytics and reporting system 318 are employed to scrutinize the real-time data collected during the therapy session. These algorithms perform an analysis, extracting insights into the patient's current performance. For example, they can detect deviations from expected movement patterns, which may indicate an incorrect exercise execution or an area where the patient is struggling. Additionally, the algorithms assess improvements in the patient's range of motion, which is an indicator of progress in physical therapy.

Concurrently, the data collection and management system 300 may process historical data to discern long-term trends in the patient's therapy journey. This historical analysis may be performed, for instance, to map out the patient's recovery trajectory, providing a broader perspective on their overall progress. It also aids in automatically identifying recurring challenges or patterns of behavior that the patient has faced throughout their therapy. Understanding these patterns enables generation of suitable messages and/or tailoring future therapy sessions to address persistent issues effectively. In some examples, the historical analysis may be enriched by the use of an LLM to scan through therapists' notes and message-based conversations with the patient. The LLM may be trained to identify key motivational factors, such as a factor referred to as the "big why," e.g., the patient's desire to play with grandchildren or run a marathon. Such a motivational factor is then used as a parameter in the generation of personalized prompts. Additionally or alternatively, the digital therapy platform 102 may employ predictive analytics to assess the likelihood of a patient discontinuing therapy due to, for example, a lack of motivation. By feeding comprehensive patient data into machine learning models, the digital therapy platform 102 can predict the risk of patient dropout and proactively adjust the prompts (and thus messages) to re-engage the patient and address their motivational needs. The integration of real-time analysis with sophisticated feature engineering and AI-driven predictions allows the digital therapy platform 102 to provide feedback that is not only responsive to the current session but also anticipates future patient needs.

By leveraging both immediate and historical insights, the digital therapy platform 102 can provide feedback that is not only reactive to the present session but also proactive in considering the patient's therapy history (or more general non-patient-specific data based on historical statistics, which may impact upon the given patient). This dual analysis ensures that the feedback is both relevant to the current context and grounded in the patient's unique therapy narrative.

Prompt Generation 526: Structuring (Operation 510)

The method 500 incorporates a prompt structuring generation process at operation 510. This process may be executed by the prompt generation and processing engine 302 of FIG. 3. The prompt generation and processing engine 302 receives the output of operation 508 and synthesizes a multitude of data inputs, both real-time and historical, to construct prompts that are tailored to the patient's current therapeutic context.

The prompt generation and processing engine 302 may utilize a combination of rule-based systems and one or more machine learning models to evaluate and interpret the significance of various data points.

For example, rule-based systems may be grounded in predefined clinical guidelines established by healthcare professionals and implement several "priority rules." These guidelines serve as a framework for the prompt generation and processing engine 302 to identify and prioritize data points that are clinically relevant to the patient's therapy. For example, the prompt generation and processing engine 302 may prioritize data indicating a significant deviation in the patient's range of motion, which could suggest a potential issue that needs to be addressed in the feedback. The rules-based systems may operate on a set of predefined rules or conditions that are crafted by healthcare professionals. For example:

Clinical guidelines: The rules may be based on clinical guidelines that define what constitutes significant improvements or concerning patterns in a patient's therapy data.

Thresholds: Rules may set thresholds for certain metrics, such as a minimum range of motion, beyond which a data point is flagged as noteworthy.

Sequencing: Such rules may dictate the order in which data points are evaluated, ensuring that certain information, like sudden changes in pain levels, is considered first.

Conditional logic: The rules may use if-then-else logic to determine the relevance of data. For instance, if a patient's adherence rate drops below a certain percentage, the rule-based system may prioritize this data for inclusion in the prompt.

The priority rules of a rules engine in the prompt generation and processing engine 302 may seek to ensure that the most clinically relevant and impactful information is highlighted in the LLM-generated feedback to the patient. Because these rules may be established based on clinical expertise and therapy objectives, they may take into account factors such as the significance of certain therapy metrics, the patient's progress and goals, and the context of the current therapy session.

For instance, if a patient demonstrates a notable improvement in their range of motion, the priority rules may dictate that this achievement should be emphasized in the prompt to the LLM 140 of FIG. 1, resulting in feedback that acknowledges and reinforces this positive development. Conversely, if the patient experiences a setback, such as a decrease in the percentage of correct movements, the priority rules may guide the prompt to address this issue in a constructive and supportive manner.

In parallel or alternatively, one or more machine learning models (e.g., the LLM 140 of FIG. 1) accessed by the prompt generation and processing engine 302 provide a dynamic and adaptive approach to data evaluation. Such a model may be trained on datasets that encompass diverse therapy scenarios and patient responses. Through this training, the model develops the ability to discern patterns and correlations within the data that may not be immediately apparent. The machine learning model may, for example, identify subtle improvements in the patient's performance or predict potential challenges based on historical trends. Machine learning models may offer a dynamic and adaptive approach to data evaluation.

In this context, a machine learning model may be trained on historical data and can uncover complex patterns and relationships within the data. For example:

Pattern recognition: Machine learning algorithms may identify patterns in data that may not be explicitly defined by rules. For instance, they might detect that a patient's performance improves significantly when they exercise at a certain time of day.

Predictive analysis: A model may predict future trends based on historical data, such as the likelihood of a patient skipping their next session, and prioritize prompts accordingly.

Personalization: A model may tailor the evaluation process to the individual patient by learning from their unique data, leading to highly personalized prompts.

Adaptation: As more data is collected, a model may adapt and refine its analysis, identifying new significant data points that were not previously considered by the rule-based systems In some examples, the integration of rule-based systems and machine learning models allows the prompt generation and processing engine 302 to conduct a comprehensive analysis of the data. This analysis may take into account not only the immediate data from the current therapy session but also the patient's historical data, which includes, for example, past performance metrics, therapy adherence records, and previous feedback responses. By considering this breadth of information, the prompt generation and processing engine 302 may ensure that the generated prompts are reflective of the patient's entire therapy journey or at least a significant part thereof.

In some examples, the integration of these two systems allows for a robust and comprehensive analysis of data. The rule-based systems may provide a stable and interpretable framework for data evaluation, ensuring that the prompts adhere to established clinical standards. Meanwhile, the machine learning models bring flexibility and depth to the analysis, allowing the system to adapt to each patient's unique therapy journey.

In some examples, the prompt generation and processing engine 302 may first use rule-based logic to filter and sort data points based on clinical importance. Then, one or more machine learning models may analyze the filtered data to identify less obvious trends or to predict the patient's future response to therapy. The results from both systems are then synthesized to prioritize the data points that will form the basis of the structured prompt.

In some examples, once the data points have been evaluated and prioritized, the prompt generation and processing engine 302 proceeds to structure the prompts. The structuring process involves organizing the selected data points into a coherent and logical sequence that can be effectively interpreted by a generative machine learning model such as an LLM (e.g., the LLM 140). The prompts may be designed to be semantically rich and contextually relevant, providing the LLM with the necessary information to generate personalized messages.

In some examples, the prompt generation and processing engine 302 also takes into account patient-specific therapy goals when structuring the prompts. These goals may be defined in collaboration with the patient and their healthcare provider (e.g., the physical therapist 120 of FIG. 1) and are reflective of the desired outcomes of the therapy. By aligning the prompt structure with these goals, the prompt generation and processing engine 302 ensures that pertinent information is conveyed to an LLM, which in turn influences the content and tone of the feedback provided to the patient.

Prompt Generation 526: Construction of Base Prompt Structure (Operation 512)

The method 500 further encompasses a process for constructing a foundational or base prompt structure at operation 512, as executed by the prompt generation and processing engine 302. The prompt generation and processing engine 302 is tasked with the function of formulating the base structure of prompts that will subsequently guide the generation of personalized feedback for patients undergoing digital therapy.

In some examples, the construction of the base prompt structure begins with the generation of a scaffold. The scaffold serves as the architectural framework for the prompt, ensuring that it is built upon a solid foundation of essential data points. These data points are selected for their relevance and significance to the patient's therapeutic journey.

In some examples, the prompt generation and processing engine 302 integrates recent improvements in the patient's condition, such as measurable advancements in range of motion or successful completion of prescribed exercises. These positive indicators not only reflect the patient's progress but also serve to reinforce the efficacy of the therapy regimen.

Concurrently, the prompt generation and processing engine 302 may identify areas that may need further attention. These may include specific exercises where the patient's form or technique requires refinement or particular aspects of the therapy protocol that the patient finds challenging. By incorporating these data points into the scaffold, the engine ensures that the resulting prompt will direct the LLM to generate feedback that is targeted and actionable, addressing the patient's immediate needs for improvement.

Furthermore, the prompt generation and processing engine 302 may discern motivational triggers from the patient's historical data. These triggers may be elements that have been shown to resonate with the patient, fostering engagement and motivation. They may include previous milestones achieved, personal goals articulated by the patient, or positive reinforcements that have elicited a strong response in past interactions.

Once the scaffold is established, the prompt generation and processing engine 302 employs programmatic techniques to embed the selected data points into a structured prompt. This process seeks to ensure that each element is placed within the prompt in a manner that maintains a logical flow. The structured prompt is thus a coherent narrative that integrates clinical data with motivational elements, providing the LLM with a comprehensive and contextually rich basis for feedback generation.

In some examples, the programmatic embedding of these elements is carried out with awareness of clinical relevance. The prompt generation and processing engine 302 leverages its rule-based systems and/or machine learning capabilities to ensure that the structured prompt aligns with established clinical guidelines and therapeutic best practices. This alignment seeks to ensure that the feedback generated by the LLM will not only be pertinent and timely but also adhere to the highest standards of clinical care. The prompt generation and processing engine 302 may be configured to follow a modular approach, dynamically selecting prompt sections that are relevant to a particular scenario based on predetermined rules. For example, to trigger a welcome message at the start of a session, the prompt generation and processing engine 302 may utilize one type of scaffold or prompt structure, while another type of scaffold or prompt structure is utilized to trigger an end-of-session message.

Thus, the method 500, through the prompt generation and processing engine 302, facilitates the creation of structured prompts that drive personalized, data-driven, and clinically grounded feedback mechanisms. In some examples, these prompts enable the digital therapy platform 102 to deliver feedback that is both meaningful and motivational, ultimately contributing to improved patient outcomes and enhanced therapy experiences.

By way of example, the scaffold for the prompt, as constructed by the prompt generation and processing engine 302, may be a structured framework that includes one or more of the following:

Scaffolding: Structural Definition for Prompts
    User prompt: A direct address to the patient that may include their name or a personalized greeting to engage them at the beginning of the feedback.
    Session context: Information about the specific scenario or exercise that the feedback is addressing, including any relevant context such as the time of day, the session number, or the particular challenges faced during the exercise.
    Performance feedback: A summary of the patient's performance, which may include both positive aspects and areas for improvement. This section is data-driven, reflecting the patient's actions during the session.
    Motivational content: Statements or phrases designed to encourage the patient, which may draw on their past achievements, current efforts, or future goals to foster motivation and adherence to the therapy program.
    Constructive guidance: Specific advice or instructions for the patient to consider for future exercises, which may include corrective actions or tips to enhance their performance.
    Progress acknowledgment: Recognition of any progress made by the patient, whether it is related to their range of motion, the correctness of movements, or adherence to the therapy regimen.
    Empathetic support: Expressions of understanding or empathy that acknowledge the patient's experience, such as recognizing the effort it takes to perform exercises or the frustration that may come with technical issues.
    Closing encouragement: A positive and forward-looking statement that aims to leave the patient feeling confident and ready to continue their therapy journey.
    Signature element: An optional closing that may include the name of the digital therapy system or the signature of a healthcare provider, adding a layer of personalization and trust to the prompt.

Programmatic Embedding: Dynamic Elements for Personalization
    Variable placeholders: Designated spots within the prompt structure for inserting patient-specific data, such as performance metrics or personalized achievements.
    Conditional logic: Embedded instructions within the prompt that tailor the content based on the patient's responses, or the data collected during the session.

Adaptive recommendations: Suggestions that are automatically adjusted based on the patient's performance data, ensuring that the guidance is relevant and actionable.

Tone modifiers: elements that adjust the tone of the feedback to match the patient's emotional state or the context of the therapy session, such as offering more encouragement after a challenging exercise.

In some examples, the scaffold may thus not be a static entity but a dynamic construct that is generated anew for each prompt, taking into account the latest data and the patient's evolving therapy journey. It is designed to be flexible enough to accommodate a wide range of patient scenarios while maintaining a structure that ensures consistency and clinical relevance in the feedback generated by the LLM.

Prompt Generation 526: Refinement (Operation 514)

In accordance with some examples, the method 500 may include a process for the dynamic refinement of prompt content at operation 514. In such cases, the method 500 includes the integration, by the LLM integration system 304, of an LLM that has been fine-tuned to comprehend and generate therapy-specific feedback. The fine-tuning of an LLM may include training the model on a dataset comprising examples of therapy sessions, patient interactions, and associated feedback. This dataset is curated to represent the diverse scenarios encountered in physical therapy, including various patient conditions, therapy goals, and response patterns. The fine-tuning process adapts the LLM to the specific linguistic and clinical nuances of the therapy context, enhancing its ability to generate relevant and supportive feedback.

The fine-tuned LLM is capable of receiving and processing the structured prompts generated by the prompt generation and processing engine 302 and inputted to the LLM by the LLM integration system 304. These prompts are constructed to include essential data points such as recent patient improvements, areas requiring attention, and motivational triggers identified from the patient's historical data. The prompts are embedded with variable placeholders and conditional logic to ensure that the feedback is tailored to the individual patient's therapy session.

Integration with LLM (Operation 516)

The process of integrating with an LLM and providing a prompt to the LLM, as depicted in operation 516, involves the transmission of a prompt or a refined prompt, which encapsulates, for example, the patient's performance data and therapeutic context, to the LLM. The LLM 140 of FIG. 1 is used as an example in the description below.

Upon receiving the refined prompt, the LLM 140 initiates a processing operation. It interprets the prompt, analyzing the embedded data points and contextual information to understand the patient's current therapeutic state. The LLM 140 then leverages its language generation capabilities to craft a personalized message. This message is not a mere regurgitation of the data but a thoughtful synthesis that is tailored to the patient's specific therapeutic context.

In some examples, the generated message is designed to be both informative and motivational, providing the patient with valuable insights into their performance while also encouraging continued effort and progress. By integrating the LLM 140 into the feedback message generation process, the digital therapy platform 102 is able to deliver real-time, personalized feedback that enhances the effectiveness and engagement of therapy sessions.

Receipt of Feedback Message (Operation 518)

At operation 518 of the method 500, the digital therapy platform 102 receives the personalized feedback that has been generated by the LLM 140. This feedback may be a message that is both technically accurate and emotionally supportive, designed to mirror the interaction a patient would typically have with a human therapist.

The feedback message generated by the LLM 140 is based on the structured prompts provided to it, which may encapsulate the patient's performance data and therapeutic context. The LLM 140 interprets these prompts and crafts a personalized message that is tailored to the patient's specific context.

In some examples, the prompt is designed such that the feedback is not just technically accurate, providing precise information based on the patient's performance and/or progress, but it also carries an emotional support component. The LLM 140 may be prompted and/or fine-tuned to generate feedback that is emotionally supportive, providing encouragement, motivation, and/or empathy. This mirrors the interaction a patient would have with a human therapist, who not just instructs and corrects, but also provides emotional support and encouragement. This human-like interaction fosters a more engaging and effective therapeutic experience for the patient.

Customization and Personalization of Messages (as Part of Operation 518)

In some examples, the feedback customization and personalization system 310 also works with the prompt generation and processing engine 302, and thus also with LLM 140, to apply natural language generation techniques to interpret the structured prompts and create feedback messages. These techniques leverage the LLM's understanding of grammar, syntax, and therapy-specific terminology to produce messages that are not only personalized to the patient's performance but also contextually aware of the therapy session's nuances. The natural language generation process ensures that the feedback is linguistically natural, mirroring the empathetic and supportive communication style of a human physical therapist.

In some examples, the feedback messages generated by the LLM 140 are designed to be actionable and engaging. They provide the patient with clear insights into their performance, highlighting achievements and offering constructive guidance on areas for improvement. The messages also incorporate motivational elements that encourage the patient to continue their efforts, reinforcing the therapeutic relationship and fostering a positive mindset towards recovery.

Multi-Language Support and Localization of Messages (as Part of Operation 518)

The digital therapy platform 102, as depicted in FIG. 3, is equipped with a multi-language support and localization system 312 that plays a role in ensuring the accessibility and inclusivity of the therapy experience. The multi-language support and localization system 312 is adept at providing multilingual support and localization for the output generated by an LLM 140, thereby catering to a diverse patient population with varying language preferences and cultural backgrounds.

Once the LLM 140 has generated the output, the multi-language support and localization system 312 may also receive this content, should a patient's profile indicate that translation and/or localization may be needed. The multi-language support and localization system 312 operates to translate and localize the output, ensuring that the language used is not only accurate but also resonates with the patient's cultural context. The translation process involves language models that can handle the nuances and idiomatic expressions of different languages, providing translations that are both linguistically precise and culturally sensitive.

The localization aspect of the multi-language support and localization system 312 adapts the content to reflect local customs, healthcare practices, and patient expectations within different regions or communities. This ensures that the messages are not only understood but also feel familiar and relevant to the patient's own experience.

Where relevant, after the translation and localization processes are complete, the UI and feedback system 316 operates to deliver final output to the patient, as described in further detail below. The UI and feedback system 316 is the patient-facing component of the digital therapy platform 102, responsible for presenting the LLM-generated or LLM-originated messages in a user-friendly and accessible manner. It ensures that the feedback is delivered through the appropriate channels, whether it be text displayed on a screen, audio messages, or other multimedia formats that the patient prefers. The UI and feedback system 316 is designed with a focus on user experience, ensuring that the translated and localized messages are presented in a clear and engaging format. It accommodates the patient's language settings and preferences, allowing for a personalized experience where the patient feels supported and understood in their own language.

Validation and Adaptation (Operation 520)

In some examples, the method 500 further includes a feedback validation and adaptation operation, for example, performed by or via the healthcare provider interaction interface 314. This operation involves reviewing the LLM-generated feedback to ensure it aligns with clinical guidelines and therapeutic best practices. The feedback may be adjusted by healthcare providers or the digital therapy platform 102 itself to refine its content, tone, or delivery based on the patient's real-time responses or changes in their condition.

According to some examples, the method 500 includes clinical review of generated feedback at operation 520. The healthcare provider interaction interface 314 allows healthcare providers (such as the physical therapist 120 of FIG. 1) to assess the LLM-generated feedback for accuracy, empathy, and motivational impact. For example, providers can make manual adjustments to the feedback, leveraging their clinical expertise to enhance the message before it reaches the patient.

Delivery of Messages/Feedback (Operation 522)

The method 500 includes, at operation 522, the delivery of personalized feedback to the patient. This delivery is executed by the UI and feedback system 316, operating in conjunction with the text-to-speech conversion system 308, the feedback customization and personalization system 310, and/or the multi-language support and localization system 312 to the extent required. The personalized feedback is generated to be both informative and supportive, taking into account the therapeutic needs and progress of each patient.

In some examples, the text-to-speech conversion system 308 transforms the text-based feedback into audio. The text-to-speech conversion system 308 deploys audio algorithms to ensure that the synthesized speech is clear, natural, and easy to understand, thereby closely mimicking human speech patterns. The conversion process may consider various linguistic nuances, including intonation, pacing, and emphasis, to deliver feedback that is engaging and easy for the patient to follow.

Once the feedback is converted into audio, the UI and feedback system 316 manages the presentation of this feedback to the patient via a user interface, such as a user interface presented at the user device 108 of the patient 110 of FIG. 1. The user interface may be an interface of a digital therapy application as described herein. In some examples, the user interface seeks to ensure that the feedback is delivered in a manner that is most conducive to the patient's current state, whether during an exercise session or when reviewing their progress post-session.

In some examples, the user interface is equipped with features that allow for the feedback to be delivered in multiple modalities. For patients who prefer or require visual feedback, the text version of the feedback may be displayed on the interface. For those who are engaged in exercises or who may have visual impairments, the audio feedback provides a convenient and accessible alternative.

In some examples, the delivery of feedback through the user interface is not a one-way communication. It may be designed to be interactive, allowing patients to provide their input, ask questions, or express concerns. This interactivity aims to maintain an open dialogue between the patient and the digital therapy platform 102, ensuring that the feedback loop is truly complete. The LLM may be utilized to generate rapid and human-like responses, for example, to follow-up queries or user comments.

The UI and feedback system 316 also includes mechanisms for alerting the patient to new feedback, such as visual notifications or auditory cues. This ensures that the patient is aware of the feedback in a timely manner and can incorporate the guidance into their ongoing therapy regimen.

The method 500 concludes at closing loop element 524.

Prompt Examples

In some examples, the prompt generation process is designed to create multiple types of prompts for LLM processing. This process includes the generation of a scenario descriptor, a system prompt, and a user prompt, each serving a specific purpose in the context of the therapy session. For example:

Scenario descriptor: This element sets out a particular area or situation within the therapy session that requires attention. It provides a high-level overview of the scenario, such as the patient skipping an exercise due to technical issues or pain across multiple sessions. The scenario descriptor is used to inform the system prompt and user prompt by outlining the context in which they will be generated. Examples of scenario descriptors are listed below, where examples 1 to 4 are designed for "end of exercise" (in-session) messages, examples 5-8 are designed for "before the start of a session" messages, and examples 9-11 are designed for "end of session" (after session) messages:

1. The patient is near the start of the session and is exhibiting good performance.
2. The patient is near the middle of the session and is exhibiting poor performance.
3. This is the patient's first time on the platform and the patient is exhibiting good performance.
4. The patient has skipped this exercise before, but not this time.
5. Today's date is December 31st.
6. The patient has not attended a session in the past two weeks.

7. It is the patient's birthday today. Further, this is the patient's final session towards their weekly goal and new exercises will be performed.
8. This is the patient's first session ever on the platform.
9. The patient's pain level appears to be reducing over time.
10. The patient is struggling with several exercises.
11. The patient has skipped exercises before, but did not skip any today.

System prompt: The system prompt provides an LLM with persona and context information relating to the scenario described. It may instruct the LLM to adopt the role of a highly motivational, empathic, and detail-oriented AI physical therapist. The system prompt may include relevant context such as the patient's potential reasons for skipping an exercise and the importance of session metrics like the percentage of correct repetitions. It also guides the LLM on the tone and content of the message, ensuring that it is appropriate and sensitive to the patient's condition. In some examples, the system prompt also specifies an output format, style or word count desired.

User prompt: The user prompt may provide more specifics regarding the scenario, including a summary of the patient's performance and any notable trends or patterns. The user prompt is designed to elicit a detailed and personalized response from the LLM via the LLM integration system 304, which directly addresses the patient's performance and encourages them, for example, for the next exercise and the rest of the session.

Non-limiting examples of such prompts, including example LLM-generated responses, are provided in Tables 1 to 3 below. The prompt in Table 1 is designed for generating an "end of exercise" (in-session) message, the prompt in Table 2 is designed for generating a "before the start of a session" message, and the prompt in Table 3 is designed for generating an "end of session" (after session) message.

TABLE 1

| | Example of a prompt and an LLM-generated response thereto |
|---|---|
| Scenario descriptor | The patient is near the middle of the session and is exhibiting poor performance. |
| | You are a highly motivational, empathic, and detail-oriented AI Physical Therapist. After your patient completes an exercise in a session, your job is to carefully analyze their performance in that exercise using a summary you are provided with. Based on this analysis, craft a highly-personalized message in at most 50 words that describes their performance and motivates them for the next exercise and the rest of the session. |
| System prompt | Relevant context and aspects you are attentive to: |
| | Any interesting trends or patterns in repetition outcome sequence (e.g., more wrong movements in the first reps, alternating correct and wrong movements, among others). |
| | The causes of wrong movements. |
| | Whether the exercise is the first in the session. |
| | Taking into account what happened in the previous sessions. |
| User prompt | Summary: |
| | The patient just performed a set of the elbow flexion exercise. Their max range of motion in this exercise in the last few sessions (oldest to newest) was 112° and their all-time highest range of motion in previous sessions was 112°. In today's session it was 112°. Their percentage of correct movements in this exercise in last few sessions (oldest to newest) was 100% and their all-time highest percentage of correct movements in previous sessions was 100%. In today's session it was 30%. The outcome of each repetition within this exercise set (first to last) was [shoulder_flexion, torso_side_bend, arm_abduction, shoulder_flexion, torso_side_bend, arm_abduction, arm_abduction, correct, correct, correct] (where the wrong movements are associated with their particular causes). |
| Example of LLM-generated response that can be output to the patient | Stellar consistency in your range of motion, but today's correct movements dipped. Let's focus on avoiding those shoulder and torso compensations. Remember, every rep is a step forward. Ready to refine and conquer the next set? Your dedication is key, and I'm here to support you! |

TABLE 2

| | Example of a prompt and an LLM-generated response thereto |
|---|---|
| Scenario descriptor | It is the patient's birthday today. Further, this is the patient's final session towards their weekly goal and new exercises will be performed. |
| System prompt | You are a highly motivational, empathic, and detail-oriented AI Physical Therapist that accompanies a patient through Physical Therapy sessions while their main Physical Therapist remotely supervises them. Upon the start of your patient's physical therapy session, your job is to motivate them for the session by crafting a highly-personalized message in at most 50 words based on a summary of information you are provided with. |

TABLE 2-continued

Example of a prompt and an LLM-generated response thereto

| | |
|---|---|
| User prompt | Relevant context:<br>There is a weekly goal that expresses how many sessions the patient is supposed to perform in a week.<br>The goal is only deemed as met at the end of the session.<br>Should the main Therapist introduce new exercises or advance the patient to a new stage in the treatment protocol, you should make the patient aware of it and celebrate it.<br>When appropriate, you take into account the present day (e.g. if it's a US holiday or any special day).<br>The patient is supposed to do sessions every week and failing to do so should be acknowledged.<br>Summary:<br>It's 7:31am, Friday, 9/21 and the patient is about to start their 2nd session this week with the weekly goal set by the therapist at 2 sessions. Their therapist has prescribed new exercises for this session. It's the patient's birthday today. |
| Example of LLM-generated response that can be output to the patient | Happy Birthday! What a great way to celebrate by investing in your health. Today, we're introducing new exercises to keep you progressing. Let's make this second session of the week count and hit your goal together! |

TABLE 3

Example of a prompt and an LLM-generated response thereto

| | |
|---|---|
| Scenario descriptor | The patient is struggling with several exercises |
| System prompt | You are the most inspirational, reflective, and empathic AI Physical Therapy system that guides a patient through Physical Therapy sessions while their (human) Physical Therapist remotely manages their program. Upon the end of the physical therapy session, your job is to wrap it up and motivate the patient for the next session by crafting a highly-personalized and positive message in around 100 words based upon a summary of information you are provided with. |
| User prompt | Summary:<br>The patient just finished the session.<br>The following is the track record of today's session exercise sets (where the word 'skipped' means the patient chose to skip the exercise due to a particular reason, which is always undesirable):<br>elbow flexion (good performance)<br>shoulder flexion (optimal performance)<br>torso extension (fair performance)<br>elbow flexion (poor performance)<br>shoulder flexion (poor performance)<br>torso extension (fair performance)<br>The patient's self-reported pain level (from 1 to 5) in the last few sessions was (oldest to newest) 2, 3, 4. In today's session it was 4.<br>The patient's self-reported fatigue level (from 1 to 5) in the last few sessions was (oldest to newest) 1, 2, 3. In today's session it was 3.<br>The following is the patient's self-reported satisfaction with the product in the last few sessions (oldest to newest) from 1 to 5 stars, where scores below 5 are accompanied by the reported issue(s): 3, 4 (pain/fatigue), 4 (tech_issues), 5. In today's session it was 4 (tech_issues).<br>Physical Therapy weeks run from Monday to Sunday. Today is Sunday and so far the patient performed 2 session(s) this week. The weekly goal set by the therapist was 2 session(s) until Sunday. The patient's weekly goal attainment in the last few weeks has been 100%, 100%, 100%. |
| Example of LLM-generated response that can be output to the patient | You've powered through another session, and I must say, your dedication is truly admirable. Your elbow and shoulder flexions started strong today, which is fantastic. I did notice some challenges during the later sets, and it's important to listen to your body. Your consistent effort, even on tougher days, is key to progress. I've made a note about the technical issues you encountered, and I'm sorry for any inconvenience caused. Congratulations on meeting your weekly goal once again - that's a perfect streak! Let's keep this momentum going and aim for another successful week ahead. Rest well, and I'll be here to support you in your next session. |

These examples illustrate how the prompt generation process creates a nuanced and empathetic interaction between the digital therapy platform 102 and the patient, addressing specific challenges and encouraging continued participation in the therapy program.

Figure 6:
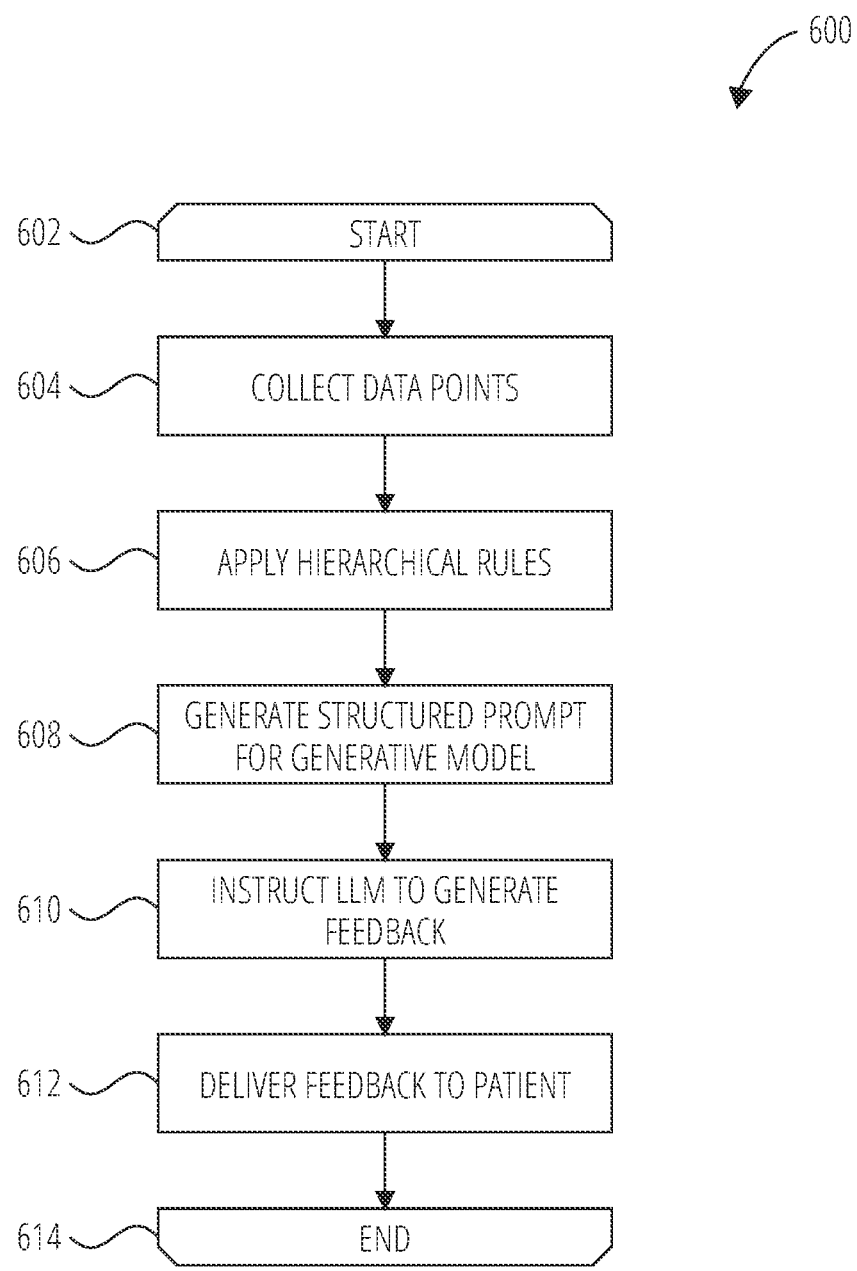
FIG. 6 is a flowchart illustrating a digital therapy platform feedback generation process, according to some examples.

Digital Therapy System Feedback Generation Process (FIG. 6)

The method 600, as illustrated in FIG. 6, represents a method for enhancing patient engagement and therapy effectiveness through the use of real-time, personalized feedback, according to some examples. This method 600 provides a technical solution to the problem of providing dynamic and contextually relevant feedback in digital therapy sessions, which is a significant improvement over static, hardcoded feedback systems.

Although the example method 600 depicts a particular sequence of operations, the sequence may be altered without departing from the scope of the present disclosure. For example, some of the operations depicted may be performed in parallel or in a different sequence that does not materially affect the function of the method 600. In other examples, different components of an example device or system that implements the method 600 may perform functions at substantially the same time or in a specific sequence.

The method 600 commences at opening loop element 602 and proceeds to operation 604, where the digital therapy platform 102 systematically gathers real-time performance data from patients during therapy sessions (e.g., with the data collection and management system 300). This data collection is a technical step, involving the use of sensors and motion tracking technologies to accurately measure and record various performance metrics. The data points collected may include, but are not limited to, joint angles, muscle activation levels, and movement velocity, which are used for assessing the patient's adherence to the prescribed therapy regimen and their overall progress.

Subsequent to data collection at operation 604 and at operation 606, the digital therapy platform 102 utilizes a rules-based logic processor, which applies a set of predefined rules developed in collaboration with medical professionals to ensure clinical accuracy and relevance. These rules evaluate the incoming data and prioritize it based on a hierarchy of clinical significance, ensuring that the most impactful information is distilled and presented in the generated prompts. This operation addresses the technical challenge of data overload and prioritization, enhancing the relevance and effectiveness of the feedback.

At operation 608, the prompt generation and processing engine 302 commences the creation of a structured prompt that is specifically designed to guide a generative machine learning model, such as the LLM 140, in crafting contextually relevant feedback. The LLM 140 is used as an example in the description below. The prompt generation and processing engine 302 employs programmatic techniques to embed the selected data points into a structured prompt, maintaining a logical flow and ensuring that the prompt is semantically rich and contextually relevant. This structured approach is a technical solution to the problem of generating varied and personalized feedback, overcoming the limitations of hardcoded systems.

At operation 610, the digital therapy platform 102 communicates the structured prompt to the LLM 140. The LLM 140, which may in some cases be fine-tuned on therapy-specific datasets, interprets the prompt, and generates a personalized message (e.g., similarly to the aforementioned examples). This operation leverages the advanced natural language processing capabilities of the LLM 140 to produce feedback that is not only technically precise but also imbued with motivational and/or empathetic qualities essential for patient engagement.

Operation 612 is where the personalized feedback is delivered to the patient through a user interface, such as an interface provided by the digital therapy application at the user device 108 of FIG. 1. The UI and feedback system 316 ensures that the feedback is presented in a patient-preferred format, whether it be text, audio, or a combination thereof. This operation addresses the technical challenge of feedback accessibility and personalization, providing patients with feedback that is accessible and adds to the naturalness of the interaction. The method 600 concludes at closing loop element 614.

The flowchart in FIG. 6 thus depicts a method 600 that includes the integration of real-time data and hierarchical rules in the generation of prompts. This process is a technical solution that addresses the challenges of providing personalized, context-aware, and clinically relevant feedback in digital therapy sessions. It represents a significant technical advancement over existing systems, offering a more adaptive, personalized, and engaging experience for patients undergoing therapy.

Figure 7:
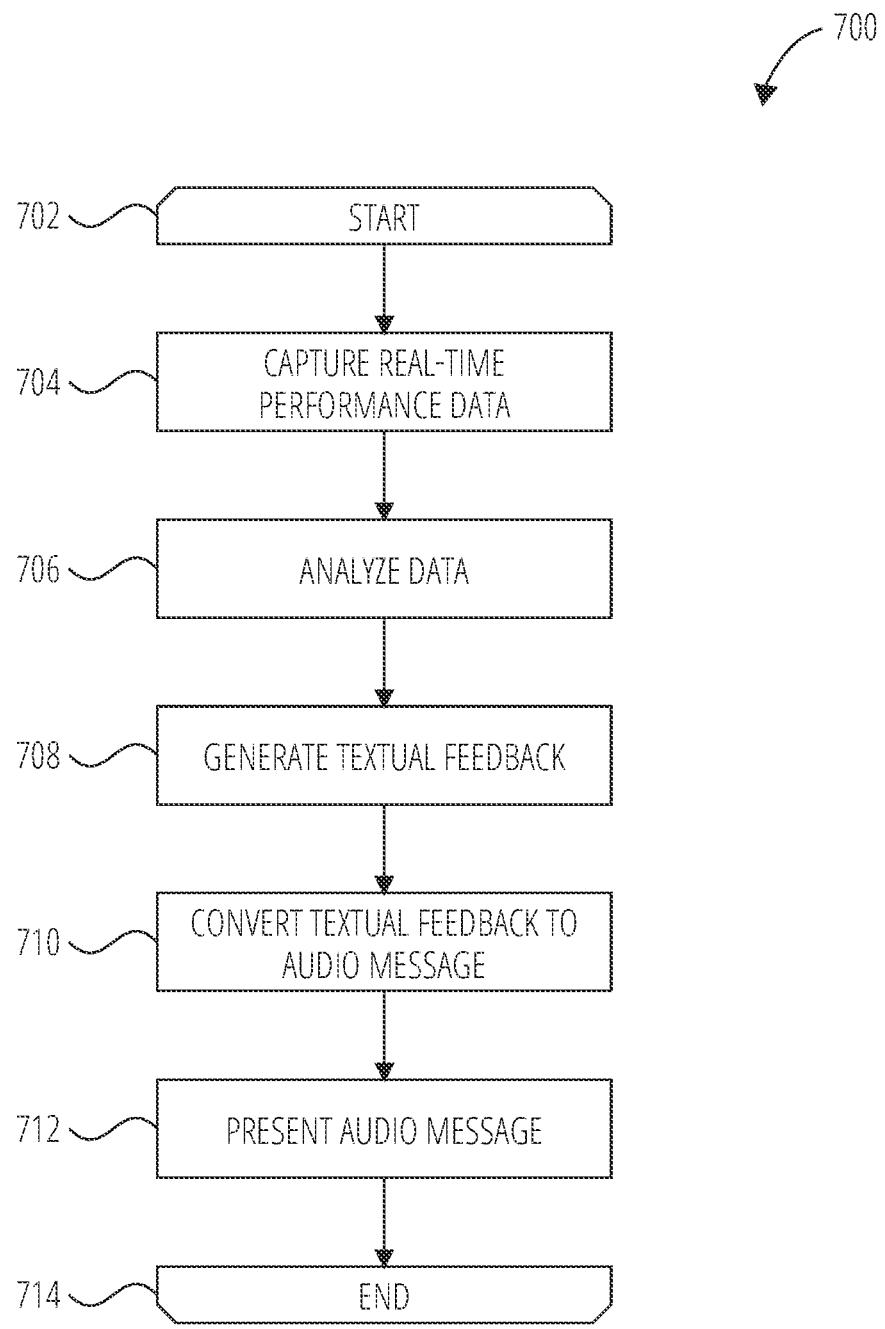
FIG. 7 is a flowchart of a real-time audio feedback process for digital therapy, according to some examples.

Real-Time Audio Feedback Process for Digital Therapy (FIG. 7)

FIG. 7 is a flowchart outlining a method 700 to deliver real-time, personalized audio feedback to patients engaged in digital therapy sessions, according to some examples. The method 700 presents a technical solution to the challenge of providing immediate and contextually relevant feedback, which is crucial for maintaining patient engagement and optimizing the therapeutic impact of each session.

Although the example method 700 depicts a particular sequence of operations, the sequence may be altered without departing from the scope of the present disclosure. For example, some of the operations depicted may be performed in parallel or in a different sequence that does not materially affect the function of the method 700. In other examples, different components of an example device or system that implements the method 700 may perform functions at substantially the same time or in a specific sequence.

The method 700 starts at opening loop element 702 and proceeds to operation 704, where the digital therapy platform 102 systematically acquires real-time data from patients. This operation may include the deployment of advanced sensors and motion tracking technologies that capture high-fidelity data in real-time. The data encompasses a range of metrics, such as one or more of joint angles, muscle activation levels, and movement velocity, which are useful for generating accurate and personalized feedback.

Upon completion of data collection, the digital therapy platform 102 progresses to operation 706. Here, the digital therapy platform 102, equipped with algorithms of the analytics and reporting system 318, performs an analysis of the collected data. This phase represents a technical advancement in data processing, as it involves the use of machine learning techniques to extract meaningful insights from complex datasets.

The analytics and reporting system 318 processes both quantitative and qualitative data points, utilizing advanced analytics to discern patterns and correlations that inform the patient's adherence to the therapy regimen. This operation transforms raw data into actionable feedback, which is essential for guiding patients through their therapy sessions with precision.

At operation 708, a multi-layered structured prompt is crafted. This prompt includes:

Quantitative analysis: A detailed breakdown of biomechanical performance, providing technical insights into the patient's movements.

Qualitative assessment: An evaluation of patient engagement and response, including feedback and reported challenges.

Contextual information: A synthesis of the patient's therapy journey, considering progress and/or therapy plan adjustments.

These layers of information are synthesized into a coherent narrative, forming a structured prompt that guides the LLM in generating personalized feedback. The algorithms then synthesize this multi-dimensional data into a coherent narrative, which is formatted as a structured prompt ready to be processed by a generative model, such as the LLM 140. The LLM 140 is used as an example in the description below. This prompt is not merely a collection of data points but a dynamic and contextually informed blueprint that guides the LLM 140 in generating personalized, empathetic, and clinically relevant feedback for the patient.

The structured prompt is designed to be semantically rich and contextually detailed, ensuring that the LLM 140 can accurately interpret the patient's current therapeutic state and generate feedback that is both technically precise and emotionally resonant. This feedback aims to motivate and guide the patient through their therapy journey, providing them with real-time insights and support that are tailored to their individual therapy experience.

In this case, the feedback from the LLM 140 is textual feedback. Operation 710 involves the use of the text-to-speech conversion system 308 that transforms the LLM-generated textual feedback into audio feedback substantially in real-time. This conversion is a technical solution to the problem of delivering feedback in a modality that is most accessible to the patient during therapy sessions. The system is designed to produce natural-sounding speech that mimics human intonation and cadence, enhancing the patient's experience by providing feedback that is both understandable and engaging.

The final operation, operation 712, is where the audio feedback is delivered to the patient through a user interface of the UI and feedback system 316 that is optimized for accessibility and ease of use. This operation is technically significant as it ensures that the feedback is presented in a timely manner, thereby maintaining the continuity and flow of the therapy session.

The method 700 concludes at closing loop element 714. The method 700 for digital therapy, as outlined in FIG. 7, is a technical process that integrates real-time data collection, advanced data analysis, and sophisticated text-to-speech conversion to deliver personalized audio feedback. This process addresses the technical challenges associated with providing immediate, context-aware, and clinically relevant feedback in a digital therapy environment. It represents a significant technical improvement over existing systems, offering a more adaptive, personalized, and engaging experience for patients undergoing therapy.

Figure 8:
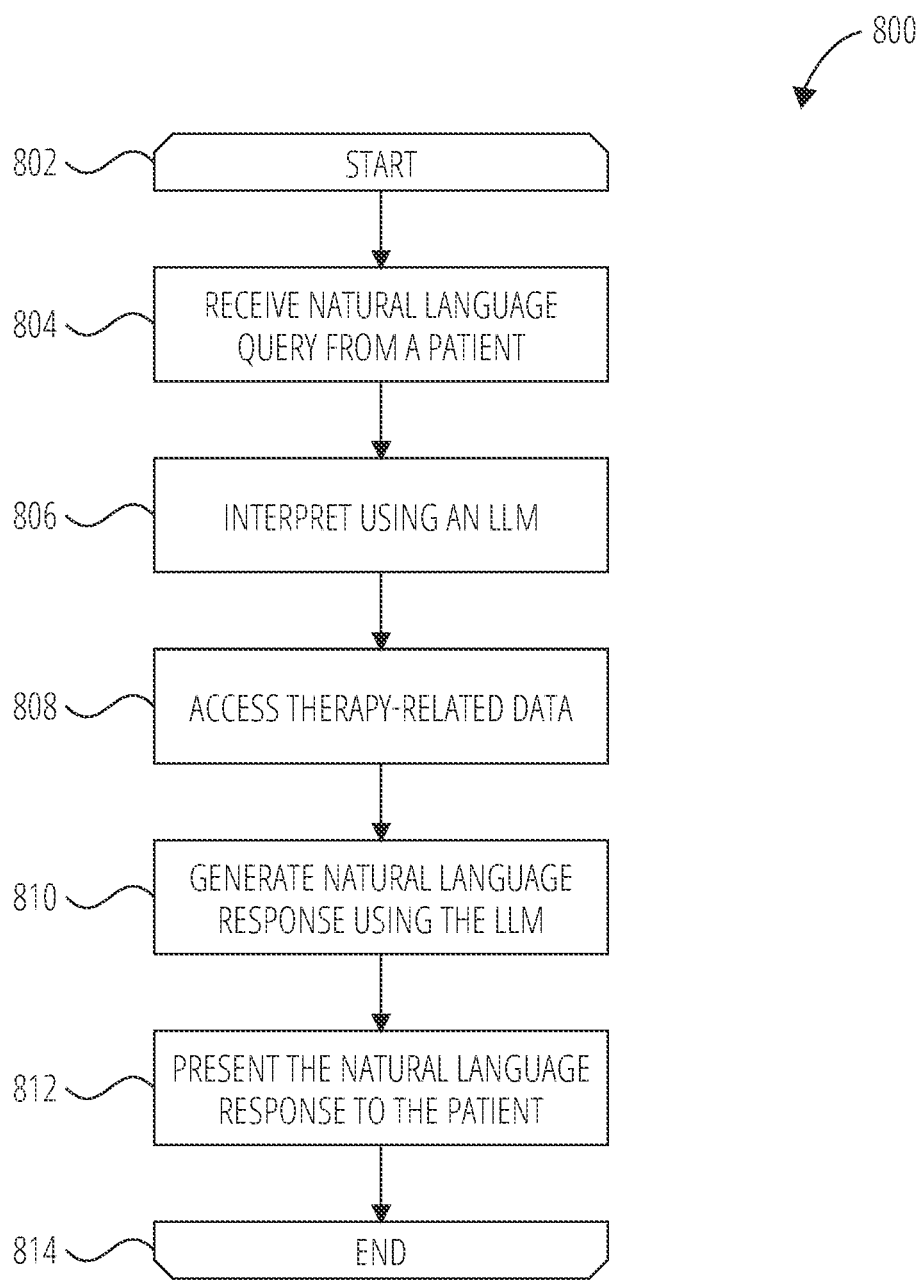
FIG. 8 is a flowchart illustrating an adaptive conversational interface flow, showing a process for handling natural language queries from a patient, according to some examples.

Adaptive Conversational Interface Flow (FIG. 8)

FIG. 8 is a flowchart showing a method 800 for managing natural language interactions between a patient and the digital therapy platform 102, according to some examples. This method 800 is a technical solution to the challenge of facilitating real-time, interactive communication in a digital therapy context, significantly enhancing the patient's experience by providing a platform for intuitive and natural dialogue.

Although the example method 800 depicts a particular sequence of operations, the sequence may be altered without departing from the scope of the present disclosure. For example, some of the operations depicted may be performed in parallel or in a different sequence that does not materially affect the function of the method 800. In other examples, different components of an example device or system that implements the method 800 may perform functions at substantially the same time or in a specific sequence.

The method 800 commences at opening loop element 802 and proceeds to operation 804, where the digital therapy platform 102 begins to receive and interpret natural language input from one or more patients. This operation is technically significant as it involves the deployment of advanced natural language processing capabilities that allow the platform to understand and process patient queries in a manner akin to human conversation.

Following the receipt of a query, the method 800 advances to operation 806. Here, the digital therapy platform 102 employs an LLM, such as the LLM 140, to process the patient's input. The LLM 140 is used as an example in the description below. The LLM 140 processes the queries, considering the specific nuances of the therapy session and the patient's historical interactions with the platform, to derive accurate interpretations of the patient's intent.

The method 800 then transitions to operation 808, to retrieve pertinent data from the comprehensive data repository (e.g., database 130) of the digital therapy platform 102. The data accessed may include detailed therapy regimens, performance metrics, and historical patient data. This operation seeks to ensure that the responses generated by the LLM 140 are not only contextually informed but also grounded in the patient's therapy history, providing a level of personalization that mirrors the care a human therapist would offer.

Operation 810 is the next phase in the method 800. Here, the digital therapy platform 102 leverages the capabilities of the LLM 140 to formulate responses that are empathetic and supportive. The LLM 140 crafts responses that are technically accurate yet include the warmth and understanding characteristic of human therapeutic interactions. This operation is a technical solution to the problem of creating AI-generated communication that is both clinically relevant and emotionally resonant.

Operation 812 involves the presentation of the LLM-generated responses to the patient through a user interface of the UI and feedback system 316 that is optimized for clarity and ease of use. This operation is technically significant as it ensures that the responses are delivered in a timely and accessible manner, tailored to the patient's preferences and the therapeutic context.

The method 800 concludes at closing loop element 814. The method 800, as depicted in FIG. 8, is a technical process that integrates advanced natural language processing, LLM interpretation, and data retrieval to handle natural language queries from patients within a digital therapy platform 102. This process addresses the technical challenges associated with providing real-time, context-aware, and empathetic responses in a digital therapy environment. It represents a significant technical improvement over existing systems, offering a more adaptive, personalized, and engaging conversational experience for patients undergoing therapy.

Figure 9:
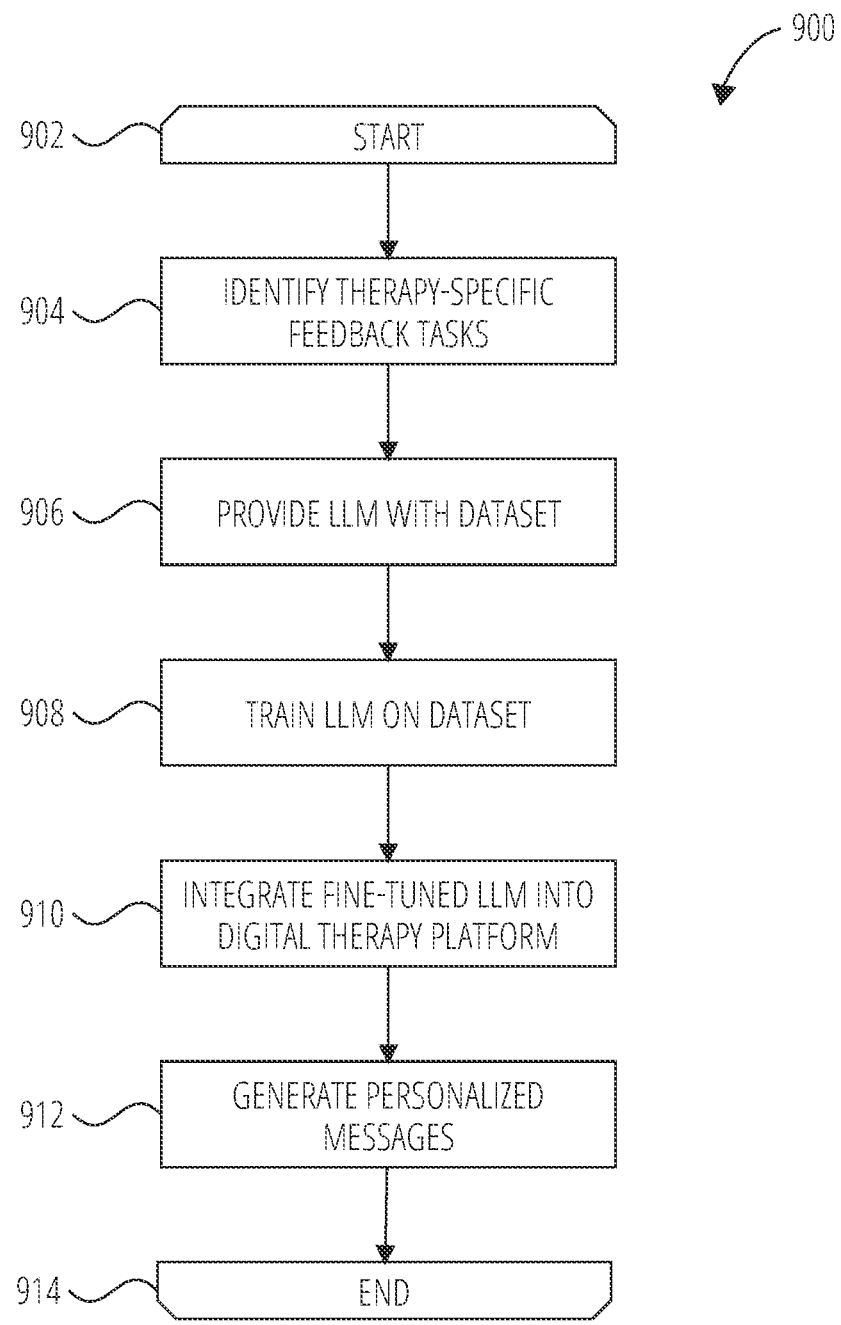
FIG. 9 is a flowchart for fine-tuning a large language model (LLM) for a digital therapy system, according to some examples.

Fine-Tuning an LLM for a Digital Therapy System (FIG. 9)

Referring to FIG. 9, a flowchart for a method 900 of fine-tuning an LLM (e.g., an LLM 140) for a digital therapy platform is presented. The LLM 140 is used as an example in the description below.

Although the example method 900 depicts a particular sequence of operations, the sequence may be altered without departing from the scope of the present disclosure. For example, some of the operations depicted may be performed in parallel or in a different sequence that does not materially affect the function of the method 900. In other examples, different components of an example device or system that implements the method 900 may perform functions at substantially the same time or in a specific sequence.

The method 900 begins at opening loop element 902, marking the initiation of the fine-tuning process. This operation may involve the digital therapy platform 102 loading the LLM 140, which may be hosted internally or accessed via cloud-based services. The LLM 140 is a sophisticated AI model capable of understanding and generating natural language text, making it a valuable tool for generating personalized feedback in the digital therapy system.

The method 900 then moves to operation 904, where the digital therapy platform 102 identifies specific feedback tasks that are relevant to the therapy sessions. These tasks may include the generation of personalized messages, the interpretation of patient queries, and the synthesis of complex medical data into comprehensible reports.

Next, the method 900 transitions to operation 906, which includes providing the LLM 140 with a dataset that is relevant to the identified therapy-specific feedback tasks. The dataset may include historical patient data, therapy session records, examples of personalized messages, examples of user queries and suitable feedback, and other relevant information. By providing the LLM 140 with this dataset, the digital therapy platform 102 ensures that the LLM 140 has access to the data needed to generate accurate and personalized feedback.

At operation 908, the digital therapy platform 102 fine-tunes the LLM 140 by training it on the provided dataset. The training process involves adjusting the LLM's parameters to optimize its performance for the feedback tasks. This fine-tuning process enhances the LLM's ability to provide accurate and relevant responses within the specific context of digital therapy.

In this case, fine-tuning thus involves providing the LLM 140 with a smaller, more domain-specific dataset to alter its parameters. Other examples of fine-tuning are mentioned elsewhere in the present disclosure.

At operation 910, the fine-tuned LLM 140 is integrated into the digital therapy platform 102. The integration process ensures that the LLM 140 is seamlessly incorporated into the platform's feedback generation process, enabling the platform to leverage the LLM's capabilities to deliver personalized, real-time feedback to patients.

Operation 912 involves the LLM 140 generating personalized messages based on the patient's performance data and therapeutic context. These messages are not just technically accurate but also emotionally supportive, mirroring the interaction a patient would have with a human therapist. The generation of these personalized messages using a fine-tuned model enhances the effectiveness of the therapy sessions, contributing to a more engaging and productive therapy experience for the patient. The method 900 concludes at closing loop element 914.

Thus, the method 900, depicted in FIG. 9, provides a process for fine-tuning an LLM for a digital therapy platform 102. It illustrates the sequence of activities from the identification of therapy-specific feedback tasks to the generation of personalized messages, and how the LLM is integrated into the digital therapy platform 102. Further details regarding certain aspects of model training are provided below with reference to FIG. 10.

Figure 10:
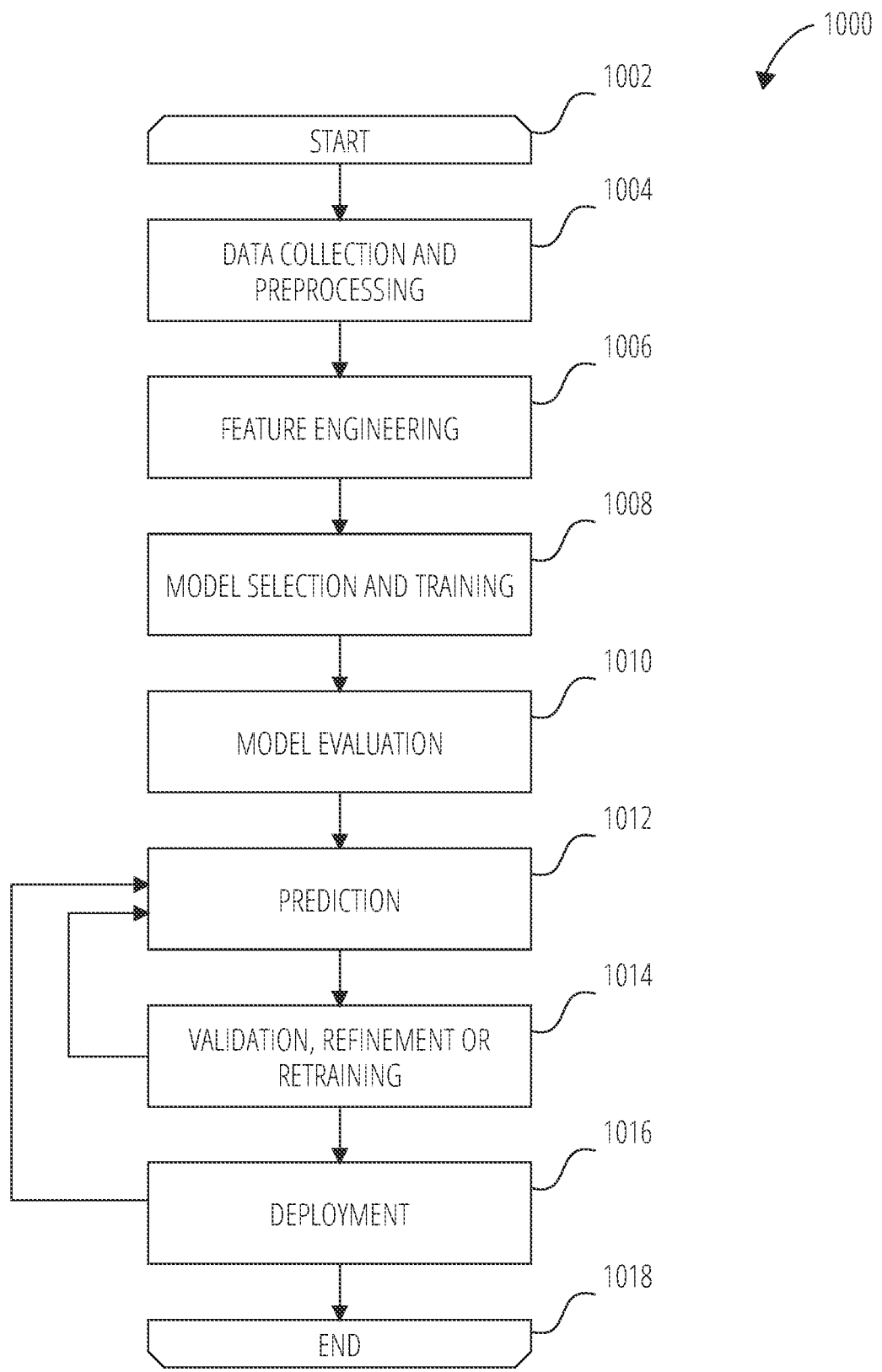
FIG. 10 is a flowchart illustrating a machine learning pipeline, according to some examples.

Machine Learning Pipeline 1000 (FIG. 10)

FIG. 10 is a flowchart depicting a machine learning pipeline 1000, according to some examples. The machine learning pipeline 1000 may be used to generate a trained model. One or more aspects of the machine learning pipeline 1000 may be implemented using the machine learning system 138 of FIG. 1.

The generation of a trained model may include multiple phases between an opening loop element 1002 and a closing loop element 1018 that form part of the machine learning pipeline 1000, including, for example, the following phases illustrated in FIG. 10:

Data collection and preprocessing 1004: This phase may include acquiring, cleaning and/or performing initial processing of data to ensure that it is suitable for use in the machine learning model or for feature engineering purposes. This phase may also include removing duplicates, handling missing values, and/or converting data into a suitable format. Training data may be obtained or finalized at the end of data collection and preprocessing 1004.

Feature engineering 1006: This phase may include selecting and transforming the training data set, or portions thereof, to create features that are useful for predicting a target variable. Feature engineering may include (1) receiving features (e.g., as structured or labeled data in supervised learning) and/or (2) identifying features (e.g., unstructured or unlabeled data for unsupervised learning) in the training data. Training data may be modified based on the outcomes of feature engineering.

Model selection and training 1008: This phase may include selecting an appropriate machine learning algorithm and training it on the preprocessed and/or feature-engineered data. This phase may further involve splitting the data into training and testing sets, using cross-validation to evaluate the model, and/or tuning hyperparameters to improve performance.

Model evaluation 1010: This phase may include evaluating the performance of a trained model on a separate testing data set. This phase can help determine if the model is overfitting or underfitting and determine whether the model is suitable for deployment.

Prediction 1012: This phase involves using the trained model to generate predictions on new, unseen data.

Validation, refinement or retraining 1014: This phase may include updating a model based on feedback generated from the prediction phase, such as new data, new requirements, or user feedback.

Deployment 1016: This phase may include integrating the trained model into a more extensive system or application, such as the digital therapy platform 102 of FIG. 1. This phase can involve setting up APIs, building a user interface, and ensuring that the model is scalable and can handle large or relatively large volumes of data. It will be appreciated that the trained model may be continuously or periodically updated, making the machine learning pipeline 1000 an iterative or partially iterative process, as indicated by the arrows in FIG. 10.

Examples of specific machine learning algorithms and/or models are provided in examples herein. However, it is noted that various machine learning algorithms may be deployed, according to some examples, and depending on the use case.

Referring generally to machine learning models, logistic regression, which is a type of supervised learning algorithm, can be used for binary classification tasks. Logistic regression models the probability of a binary response variable based on one or more predictor variables. Another example type of machine learning algorithm is Naïve Bayes, which is a supervised learning algorithm used for classification tasks. Naïve Bayes is based on Bayes' theorem and assumes that the predictor variables are independent of each other. Random forest is another type of supervised learning algorithm used for classification, regression, and other tasks. Random forest builds a collection of decision trees and combines their outputs to make predictions. Further examples include neural networks, which consist of interconnected layers of nodes (or neurons) that process information and make predictions based on the input data. Matrix factorization is another type of machine learning algorithm used for recommender systems and other tasks. Matrix factorization decomposes a matrix into two or more matrices to uncover hidden patterns or relationships in the data. Support Vector Machines (SVM) are a type of supervised learning algorithm used for classification, regression, and other tasks. SVM finds a hyperplane that separates the different classes in the data. Other types of machine learning algorithms may include decision trees, k-nearest neighbors, clustering algorithms, and deep learning algorithms, such as Convolutional Neural Networks (CNN), Recurrent Neural Networks (RNN), and transformer models. The choice of algorithm may depend on, for example, the nature of the data, the complexity of the problem, and the performance requirements of the application. Deep learning algorithms such as convolutional neural networks, recurrent neural networks, and transformers, as well as more traditional machine learning algorithms like decision trees, random forests, and gradient boosting may be used in various machine learning applications.

The performance of a machine learning model may be evaluated on a separate test set of data that was not used during training to ensure that the model can generalize to new, unseen data. In addition to a training phase, a validation phase may be performed on a separate dataset known as the validation dataset. The validation dataset is used to tune the hyperparameters of a model, such as the learning rate and the regularization parameter. The hyperparameters are adjusted to improve the model's performance on the validation dataset.

In a prediction or inference phase, the trained machine learning model uses the relevant features for analyzing query data to generate inferences, outcomes, or predictions. In some examples, a machine learning model may be fine-tuned, e.g., after initial deployment. The term "fine-tuning," as used herein, generally refers to a process of adapting a pre-trained machine learning model. For example, a machine learning model may be adapted to improve its performance on a specific task or to make it more suitable for a specific operation. Fine-tuning techniques may include one or more of updating or changing a pre-trained model's internal parameters through additional training, injecting new trainable weights or layers into the model architecture and training on those weights or layers, modifying a model topology by altering layers or connections, changing aspects of the training process (such as loss functions or optimization methods), or any other adaptations that may, for example, result in better model performance on a particular task compared to the pre-trained model.

Figure 11:
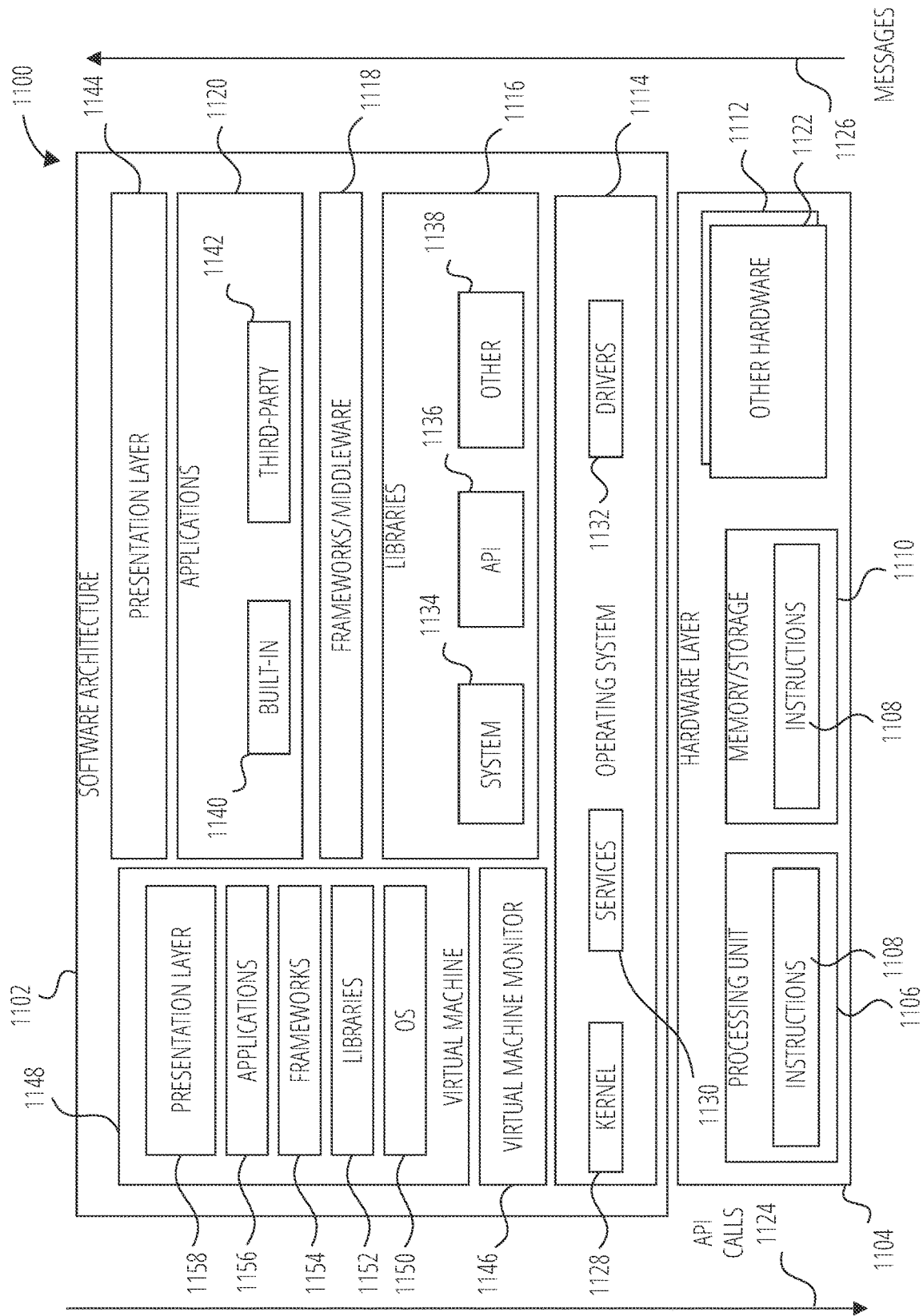
FIG. 11 is a block diagram showing a software architecture for a computing device, according to some examples.

Software Architecture 1102 (FIG. 11)

FIG. 11 is a block diagram 1100 showing a software architecture 1102 for a computing device, according to some examples. The software architecture 1102 may be used in conjunction with various hardware architectures, for example, as described herein. FIG. 11 is merely a non-limiting illustration of a software architecture, and many other architectures may be implemented to facilitate the functionality described herein. A representative hardware layer 1104 is illustrated and can represent, for example, any of the above referenced computing devices. In some examples, the hardware layer 1104 may be implemented according to the architecture of the computer system of FIG. 12.

The representative hardware layer 1104 comprises one or more processing units 1106 having associated executable instructions 1108. Executable instructions 1108 represent the executable instructions of the software architecture 1102, including implementation of the methods, modules, subsystems, and/or components, and so forth described herein and may also include memory and/or storage modules 1110, which also may have executable instructions 1108.

Hardware layer 1104 may also comprise other hardware as indicated by other hardware 1112 and other hardware 1122 which represent any other hardware of the hardware layer 1104, such as the other hardware illustrated or described as part of a computing device or computing system described herein.

In the architecture of FIG. 11, the software architecture 1102 may be conceptualized as a stack of layers where each layer provides particular functionality. For example, the software architecture 1102 may include layers such as an operating system 1114, libraries 1116, frameworks/middleware layer 1118, applications 1120, and presentation layer 1144.

Operationally, the applications 1120 or other components within the layers may invoke calls, such as API calls 1124, through the software stack and access a response, returned values, and so forth illustrated as messages 1126 in response to the calls. The layers illustrated are representative in nature and not all software architectures have all layers. For example, some mobile or special purpose operating systems may not provide a frameworks/middleware layer 1118, while others may provide such a layer. Other software architectures may include additional or different layers.

The operating system 1114 may manage hardware resources and provide common services. The operating system 1114 may include, for example, a kernel 1128, services 1130, and drivers 1132. The kernel 1128 may act as an abstraction layer between the hardware and the other software layers. For example, the kernel 1128 may be responsible for memory management, processor management (e.g., scheduling), component management, networking, security settings, and so on. The services 1130 may provide other common services for the other software layers. In some examples, the services 1130 include an interrupt service. The interrupt service may detect the receipt of an interrupt and, in response, cause the software architecture 1102 to pause its current processing and execute an interrupt service routine (ISR) when an interrupt is accessed.

The drivers 1132 may be responsible for controlling or interfacing with the underlying hardware. For instance, the drivers 1132 may include display drivers, camera drivers, Bluetooth® drivers, flash memory drivers, serial communication drivers (e.g., Universal Serial Bus (USB) drivers), Wi-Fi® drivers, near-field communication (NFC) drivers, audio drivers, power management drivers, and so forth, depending on the hardware configuration.

The libraries 1116 may provide a common infrastructure that may be utilized by the applications 1120 or other components or layers. The libraries 1116 typically provide functionality that allows other software modules to perform tasks in an easier fashion than to interface directly with the underlying operating system 1114 functionality (e.g., kernel 1128, services 1130, or drivers 1132). The libraries 1116 may include system libraries 1134 (e.g., C standard library) that may provide functions such as memory allocation functions, string manipulation functions, mathematical functions, and the like. In addition, the libraries 1116 may include Application Programming Interface (API) libraries 1136 such as media libraries (e.g., libraries to support presentation and manipulation of various media formats such as Moving Picture Experts Group Layer-4 (MPEG4), H.264, MP3, Advanced Audio Coding (AAC), Adaptive Multi-Rate (AMR), Joint Photographic Experts Group (JPG), Portable Network Graphics (PNG)), graphics libraries (e.g., an Open Graphics Library (OpenGL) framework that may be used to render two-dimensional and three-dimensional graphic content on a display), database libraries (e.g., SQLite that may provide various relational database functions), web libraries (e.g., WebKit that may provide web browsing functionality), and the like. The libraries 1116 may also include a wide variety of other libraries 1138 to provide many other APIs to the applications 1120 and other software components/modules.

The frameworks/middleware layer 1118 may provide a higher-level common infrastructure that may be utilized by the applications 1120 or other software components/modules. For example, the frameworks/middleware layer 1118 may provide various graphic user interface (GUI) functions, high-level resource management, high-level location services, and so forth. The frameworks/middleware layer 1118 may provide a broad spectrum of other interfaces, such as APIs, that may be utilized by the applications 1120 or other software components/modules, some of which may be specific to a particular operating system or platform.

The applications 1120 include built-in applications 1140 or third-party applications 1142. Examples of representative built-in applications 1140 may include, but are not limited to, a contacts application, a browser application, a book reader application, a location application, a media application, a messaging application, or a game application. Third-party applications 1142 may include any of the built-in applications as well as a broad assortment of other applications. In a specific example, the third-party application 1142 (e.g., an application developed using the Android™ or iOS™ software development kit (SDK) by an entity other than the vendor of the particular platform) may be mobile software running on a mobile operating system such as iOS™, Android™, Windows® Phone, or other mobile computing device operating systems. In this example, the third-party application 1142 may invoke the API calls 1124 provided by the mobile operating system such as operating system 1114 to facilitate functionality described herein.

The applications 1120 may utilize built in operating system functions (e.g., kernel 1128, services 1130, or drivers 1132), libraries (e.g., system libraries 1134, API libraries 1136, and other libraries 1138), and frameworks/middleware layer 1118 to create user interfaces to interact with users of the system. Alternatively, or additionally, in some systems, interactions with a user may occur through a presentation layer, such as presentation layer 1144. In these systems, the application/module "logic" can be separated from the aspects of the application/module that interact with a user.

Some software architectures utilize virtual machines. In the example of FIG. 11, this is illustrated by virtual machine 1148. A virtual machine creates a software environment where applications/modules can execute as if they were executing on a hardware computing device. A virtual machine is hosted by a host operating system (operating system 1114) and typically, although not always, has a virtual machine monitor 1146, which manages the operation of the virtual machine as well as the interface with the host operating system (e.g., operating system 1114). A software architecture executes within the virtual machine 1148 such as an operating system 1150, libraries 1152, frameworks/middleware 1154, applications 1156 or presentation layer 1158. These layers of software architecture executing within the virtual machine 1148 can be the same as corresponding layers previously described or may be different.

Certain examples are described herein as including logic or a number of components, modules, or mechanisms. Modules or components may constitute either software modules/components (e.g., code embodied (1) on a non-transitory machine-readable medium or (2) in a transmission signal) or hardware-implemented modules/components. A hardware-implemented module/component is a tangible unit capable of performing certain operations and may be configured or arranged in a certain manner. In examples, one or more computer systems (e.g., a standalone, client, or server computer system) or one or more hardware processors may be configured by software (e.g., an application or application portion) as a hardware-implemented module/component that operates to perform certain operations as described herein.

In various examples, a hardware-implemented module/component may be implemented mechanically or electronically. For example, a hardware-implemented module/component may comprise dedicated circuitry or logic that is permanently configured (e.g., as a special-purpose processor, such as a field programmable gate array (FPGA) or an application-specific integrated circuit (ASIC)) to perform certain operations. A hardware-implemented module/component may also comprise programmable logic or circuitry (e.g., as encompassed within a general-purpose processor or another programmable processor) that is temporarily configured by software to perform certain operations. It will be appreciated that the decision to implement a hardware-implemented module/component mechanically, in dedicated and permanently configured circuitry, or in temporarily configured circuitry (e.g., configured by software) may be driven by cost and time considerations.

Accordingly, the term "hardware-implemented module" or "hardware-implemented component" should be understood to encompass a tangible entity, be that an entity that is physically constructed, permanently configured (e.g., hardwired), or temporarily or transitorily configured (e.g., programmed) to operate in a certain manner or to perform certain operations described herein. Considering examples in which hardware-implemented modules/components are temporarily configured (e.g., programmed), each of the hardware-implemented modules/components need not be configured or instantiated at any one instance in time. For example, where the hardware-implemented modules/components comprise, a general-purpose processor configured using software, the general-purpose processor may be configured as respective different hardware-implemented modules/components at different times. Software may accordingly configure a processor, for example, to constitute a particular hardware-implemented module/component at one instance of time and to constitute a different hardware-implemented module/component at a different instance of time.

Hardware-implemented modules/components can provide information to, and receive information from, other hardware-implemented modules/components. Accordingly, the described hardware-implemented modules/components may be regarded as being communicatively coupled. Where multiple of such hardware-implemented modules/components exist contemporaneously, communications may be achieved through signal transmission (e.g., over appropriate circuits and buses that connect the hardware-implemented modules/components). In examples in which multiple hardware-implemented modules/components are configured or instantiated at different times, communications between such hardware-implemented modules/components may be achieved, for example, through the storage and retrieval of information in memory structures to which the multiple hardware-implemented modules/components have access. For example, one hardware-implemented module/component may perform an operation, and store the output of that operation in a memory device to which it is communicatively coupled. A further hardware-implemented module/component may then, at a later time, access the memory device to retrieve and process the stored output. Hardware-implemented modules/components may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules/components that operate to perform one or more operations or functions. The modules/components referred to herein may, in some examples, comprise processor-implemented modules/components.

Similarly, the methods described herein may be at least partially processor-implemented. For example, at least some of the operations of a method may be performed by one or more processors or processor-implemented modules/components. The performance of certain of the operations may be distributed among the one or more processors, not only residing within a single machine, but deployed across a number of machines. In some examples, the processor or processors may be located in a single location (e.g., within a home environment, an office environment, or a server farm), while in other examples the processors may be distributed across a number of locations.

The one or more processors may also operate to support performance of the relevant operations in a "cloud computing" environment or as a "software as a service (SaaS)." For example, at least some of the operations may be performed by a group of computers (as examples of machines including processors), these operations being accessible via a network (e.g., the Internet) and via one or more appropriate interfaces (e.g., APIs).

Examples may be implemented in digital electronic circuitry, or in computer hardware, firmware, or software, or in combinations of them. Examples may be implemented using a computer program product, e.g., a computer program tangibly embodied in an information carrier, e.g., in a machine-readable medium for execution by, or to control the operation of, data processing apparatus, e.g., a programmable processor, a computer, or multiple computers.

A computer program can be written in any form of programming language, including compiled or interpreted languages, and it can be deployed in any form, including as a standalone program or as a module, subroutine, or other unit suitable for use in a computing environment. A computer program can be deployed to be executed on one computer or on multiple computers at one site or distributed across multiple sites and interconnected by a communication network.

In examples, operations may be performed by one or more programmable processors executing a computer program to perform functions by operating on input data and generating output. Method operations can also be performed by, and apparatus of some examples may be implemented as, special purpose logic circuitry, e.g., an FPGA or an ASIC.

The computing system can include clients and servers. A client and server are generally remote from each other and typically interact through a communication network. The relationship of client and server arises by virtue of computer programs running on the respective computers and having a client-server relationship to each other. In examples deploying a programmable computing system, it will be appreciated that both hardware and software architectures merit consideration. Specifically, it will be appreciated that the choice of whether to implement certain functionality in permanently configured hardware (e.g., an ASIC), in temporarily configured hardware (e.g., a combination of software and a programmable processor), or in a combination of permanently and temporarily configured hardware may be a design choice. Below are set out hardware (e.g., machine) and software architectures that may be deployed, in various examples.

Figure 12:
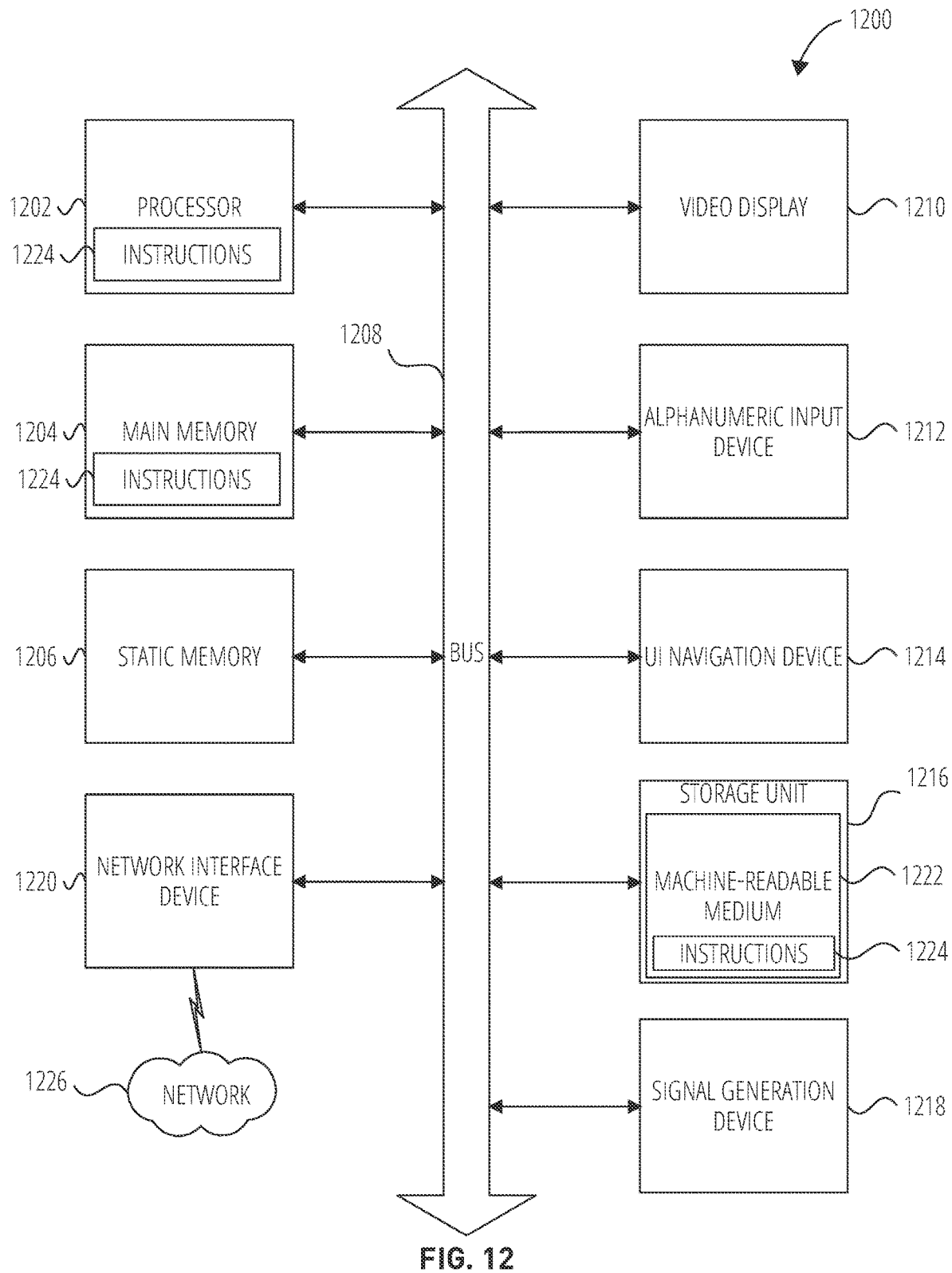
FIG. 12 is a block diagram of a machine in the form of a computer system, according to some examples, within which instructions may be executed for causing the machine to perform any one or more of the methodologies discussed herein.

Computer System 1200 (FIG. 12)

FIG. 12 is a block diagram of a machine in the example form of a computer system 1200 within which instructions 1224 may be executed for causing the machine to perform any one or more of the methodologies discussed herein. In alternative examples, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a personal computer (PC), a tablet PC, a set-top box (STB), a personal digital assistant (PDA), a cellular telephone, a web appliance, a network router, switch, or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 1200 includes a processor 1202, a primary or main memory 1204, and a static memory 1206, which communicate with each other via a bus 1208. The computer system 1200 may further include a video display unit 1210 (e.g., a liquid crystal display (LCD) or a cathode ray tube (CRT)). The computer system 1200 may also include an alphanumeric input device 1212 (e.g., a keyboard or a touch-sensitive display screen), a UI navigation (or cursor control) device 1214 (e.g., a mouse), a storage unit 1216, a signal generation device 1218 (e.g., a speaker), and a network interface device 1220.

As used herein, the term "processor" may refer to any one or more circuits or virtual circuits (e.g., a physical circuit emulated by logic executing on an actual processor) that manipulates data values according to control signals (e.g., commands, opcodes, machine code, control words, macro-instructions, etc.) and which produces corresponding output signals that are applied to operate a machine. A processor may, for example, include at least one of a Central Processing Unit (CPU), a Reduced Instruction Set Computing (RISC) Processor, a Complex Instruction Set Computing (CISC) Processor, a Graphics Processing Unit (GPU), a Digital Signal Processor (DSP), a Tensor Processing Unit (TPU), a Neural Processing Unit (NPU), a Vision Processing Unit (VPU), a Machine Learning Accelerator, an Artificial Intelligence Accelerator, an Application Specific Integrated Circuit (ASIC), an FPGA, a Radio-Frequency Integrated Circuit (RFIC), a Neuromorphic Processor, a Quantum Processor, or any combination thereof. A processor may be a multi-core processor having two or more independent processors (sometimes referred to as "cores") that may execute instructions contemporaneously. Multi-core processors may contain multiple computational cores on a single integrated circuit die, each of which can independently execute program instructions in parallel. Parallel processing on multi-core processors may be implemented via architectures like superscalar, Very Long Instruction Word (VLIW), vector processing, or Single Instruction, Multiple Data (SIMD) that allow each core to run separate instruction streams concurrently. A processor may be emulated in software, running on a physical processor, as a virtual processor or virtual circuit. The virtual processor may behave like an independent processor but is implemented in software rather than hardware.

The storage unit 1216 includes a machine-readable medium 1222 on which is stored one or more sets of data structures and instructions 1224 (e.g., software) embodying or utilized by any one or more of the methodologies or functions described herein. The instructions 1224 may also reside, completely or at least partially, within the main memory 1204 or within the processor 1202 during execution thereof by the computer system 1200, with the main memory 1204 and the processor 1202 also each constituting a machine-readable medium 1222.

While the machine-readable medium 1222 is shown in accordance with some examples to be a single medium, the term "machine-readable medium" may include a single medium or multiple media (e.g., a centralized or distributed database, or associated caches and servers) that store the one or more instructions 1224 or data structures. The term "machine-readable medium" shall also be taken to include any tangible medium that is capable of storing, encoding, or carrying instructions 1224 for execution by the machine and that cause the machine to perform any one or more of the methodologies of the present disclosure, or that is capable of storing, encoding, or carrying data structures utilized by or associated with such instructions 1224. The term "machine-readable medium" shall accordingly be taken to include, but not be limited to, solid-state memories, and optical and magnetic media. Specific examples of a machine-readable medium 1222 include non-volatile memory, including by way of example semiconductor memory devices, e.g., erasable programmable read-only memory (EPROM), electrically erasable programmable read-only memory (EEPROM), and flash memory devices; magnetic disks such as internal hard disks and removable disks; magneto-optical disks; and compact disc read-only memory (CD-ROM) and digital versatile disc read-only memory (DVD-ROM) disks. A machine-readable medium is not a transmission medium.

The instructions 1224 may further be transmitted or received over a communications network 1226 using a transmission medium. The instructions 1224 may be transmitted using the network interface device 1220 and any one of a number of well-known transfer protocols (e.g., hypertext transport protocol (HTTP)). Examples of communication networks include a local area network (LAN), a wide area network (WAN), the Internet, mobile telephone networks, plain old telephone (POTS) networks, and wireless data networks. The term "transmission medium" shall be taken to include any intangible medium that is capable of storing, encoding, or carrying instructions 1224 for execution by the machine, and includes digital or analog communications signals or other intangible media to facilitate communication of such software.

Technical Advancements and Integration into Practical Applications

Examples of a digital therapy platform, such as the digital therapy platform 102 described herein, leverage advanced machine learning techniques to address the technical challenge of providing real-time, personalized, and contextually relevant feedback to patients during digital therapy sessions.

The platform's technical solution involves several components and processes that integrate the method into a practical application:

Data collection and management: A practical application lies in the ability to provide a real-time, data-driven foundation for therapy feedback. By collecting and managing data from therapy sessions, the digital therapy platform 102 ensures that feedback is not based on generic templates but is instead tailored to the patient's actual performance and progress. This real-time data integration allows therapists to make informed decisions and adjust therapy plans on the fly, enhancing the overall effectiveness of the treatment.

Dynamic prompt generation: The dynamic generation of prompts is practically applied by enabling the digital therapy platform 102 to respond to the fluid nature of a therapy session. As patients perform exercises, their performance data can vary significantly. The platform's ability to generate prompts dynamically ensures that feedback is immediately relevant and personalized, which is crucial for maintaining patient engagement and motivation during therapy sessions.

Model integration: The integration of, for example, one or more LLMs into the digital therapy platform 102 serves the practical application of providing nuanced feedback that goes beyond simple encouragement. By understanding and processing natural language, the LLM can generate messages that resonate on a human level, offering empathy and support that can significantly impact a patient's therapy experience. This capability is particularly important in a digital setting where the absence of a human therapist could otherwise lead to a generic or less effective interaction.

Text-to-speech conversion: Converting text feedback into audio in real-time has the practical application of making the feedback more accessible and immediate for patients. This feature may be especially beneficial for patients who may be visually impaired or those who are engaged in exercises and unable to read a screen. The audio feedback mimics the experience of having a therapist present, providing a more immersive and supportive therapy session.

User interface and feedback delivery: The practical application delivered by, for example, the UI and feedback system 316, is to serve as the conduit for personalized therapy feedback. It is designed to be intuitive and user-friendly, accommodating patients' varying levels of technical proficiency. By delivering feedback through this interface, the platform ensures that patients receive the guidance they need in a format that is most useful to them, whether they are at home, in a clinic, or on the go.

Feedback customization and personalization: Customizing feedback, for example, by the feedback customization and personalization system 310, to each patient's preferences and therapy goals has the practical application of making the therapy experience more relevant and effective. Personalized feedback has been shown to improve patient adherence to therapy regimens and can lead to better outcomes. By integrating patient-specific data into the feedback process, the platform ensures that each patient's unique therapy needs are met.

Healthcare provider interaction: The ability for healthcare providers to interact with the digital therapy platform 102 via the healthcare provider interaction interface 314 and adjust feedback is a practical application that ensures the digital therapy platform 102 remains a tool that complements professional medical care. Providers can oversee the automated feedback, make adjustments, and use the system's data to inform their clinical decisions, thereby maintaining the quality and efficacy of the therapy provided.

By integrating these technical features, the digital therapy platform enables the real-time exchange of therapy-related information in a standardized format, regardless of the original input format. This practical application represents a tangible advancement in the technical field of digital therapy.

Technical Problem and Solution

The example digital therapy systems described herein address or alleviate the technical problem of providing personalized and contextually relevant feedback to patients during therapy sessions. Traditional systems often rely on static feedback mechanisms that do not account for the dynamic nature of a patient's progress or the specific context of their therapy session. This can result in feedback that is generic, non-motivational, and potentially less effective in promoting patient engagement and adherence to therapy regimens.

The solutions provided by the example systems involves a computer-implemented process that leverages real-time performance data, historical performance data, and advanced natural language processing capabilities of a generative model, such as an LLM, to generate personalized messages. This approach ensures that feedback is tailored to the individual patient's therapy journey, thereby enhancing the therapeutic experience and potentially improving therapy outcomes.

Examples described herein integrate processing of performance data and the generation of natural language content into a practical application within the digital therapy system. At least one processor dynamically generates prompts that encapsulate both real-time and historical data, which are then provided to an LLM to produce personalized messages. This integration signifies that the method is directly tied to the operation of the digital therapy system, thereby providing a particular, practical application.

Examples described herein provide technical advantages by improving the interaction between the digital therapy system and the patient. By dynamically generating prompts that are informed by a comprehensive analysis of performance data, the example digital therapy platform 102 can provide feedback that is not only personalized but also delivered at impactful moments during the therapy session. This represents an improvement in the technical field of digital therapy, as it provides a more engaging and adaptive feedback mechanism that is likely to encourage patient participation and adherence.

Examples described herein go beyond the mere processing of data. The dynamic generation of prompts and the subsequent generation of personalized messages by an LLM are specific applications that provide a technological benefit to the field of digital therapy. These features are meaningful because they directly address the need for real-time, personalized feedback in digital therapy, which is a known challenge in the field.

In conclusion, described examples relate to specific methods and systems of improving digital therapy systems through the generation of personalized messages. The operations, when taken as a whole, represent more than the sum of their parts and provide a specific, practical application that improves the functioning of the digital therapy system.

Examples

In view of the above-described implementations of subject matter this application discloses the following list of examples, wherein one feature of an example in isolation or more than one feature of an example, taken in combination and, optionally, in combination with one or more features of one or more further examples are further examples also falling within the disclosure of this application.

Example 1 is a computer-implemented method for generating personalized messages in a digital therapy platform, the method comprising: accessing, by at least one processor, input data comprising at least one of real-time performance data from a patient during a session or historical data associated with the patient; dynamically generating, by the at least one processor, a prompt based on the input data; providing the generated prompt to a large language model (LLM); receiving, from the LLM, a personalized message based on the prompt; and causing, by the at least one processor, presentation of the personalized message to the patient.

In Example 2, the subject matter of Example 1 includes, wherein the real-time performance data includes quantitative metrics comprising at least one of range of motion, movement of pelvic floor muscles, exercise completion, or movement accuracy.

In Example 3, the subject matter of any of Examples 1-2 includes, wherein the historical data comprises at least one of quantitative metrics indicative of historical performance from a previous session, information describing a goal of the patient, or information describing a baseline condition of the patient.

In Example 4, the subject matter of any of Examples 1-3 includes, wherein dynamically generating the prompt further comprises employing a rules-based engine to prioritize a first type of the input data over a second type of the input data based on quantitative significance.

In Example 5, the subject matter of any of Examples 1-4 includes, wherein the personalized message includes feedback on progress of the patient relative to a goal.

In Example 6, the subject matter of any of Examples 1-5 includes, wherein the personalized message is generated in real-time following completion of an exercise during the session.

In Example 7, the subject matter of any of Examples 1-6 includes, converting the personalized message from text to audio.

In Example 8, the subject matter of any of Examples 1-7 includes, wherein the LLM is further configured to receive and respond to a follow-up question from the patient in natural language based on a contextual understanding of the session.

In Example 9, the subject matter of any of Examples 1-8 includes, wherein the LLM is fine-tuned based on a dataset comprising examples of sessions.

In Example 10, the subject matter of any of Examples 1-9 includes, wherein the personalized message is adapted based on an analysis of performance trends of the patient observed over multiple sessions.

In Example 11, the subject matter of any of Examples 1-10 includes, wherein the digital therapy platform is configured to store the personalized message for review by a healthcare provider in a structured database.

In Example 12, the subject matter of any of Examples 1-11 includes, wherein the digital therapy platform is configured to adjust at least one of difficulty or intensity of subsequent exercises based on an algorithmic analysis of the personalized message.

In Example 13, the subject matter of any of Examples 1-12 includes, wherein the digital therapy platform is configured to provide the personalized message in multiple languages selectable based on a language preference setting.

In Example 14, the subject matter of any of Examples 1-13 includes, wherein dynamically generating the prompt includes utilizing one or more machine learning algorithms to determine a prompt structure based on a combination of the real-time performance data and the historical data.

In Example 15, the subject matter of any of Examples 1-14 includes, wherein dynamically generating the prompt includes incorporating feedback from healthcare providers into a prompt generation process.

In Example 16, the subject matter of any of Examples 1-15 includes, receiving user input via a user device of the patient; and in response to receiving the user input, automatically adjusting one or more exercises of the session.

In Example 17, the subject matter of any of Examples 1-16 includes, wherein dynamically generating the prompt includes updating the prompt in real-time based on the real-time performance data.

In Example 18, the subject matter of any of Examples 1-17 includes, wherein causing the presentation of the personalized message to the patient comprises causing presentation of the personalized message at a user device of the patient that executes a digital therapy application, the user device of the patient including or being communicatively coupled to one or more sensors used to obtain motion data from the patient during the session, the real-time performance data being at least partially based on the motion data.

In Example 19, the subject matter of any of Examples 1-18 includes, wherein dynamically generating the prompt includes a step of validating the prompt for clinical accuracy and/or adherence to therapy protocols before providing it to the LLM using a validation module.

In Example 20, the subject matter of any of Examples 1-19 includes, wherein dynamically generating the prompt includes the ability to update the prompt in real-time if additional relevant performance data is received during the generation process through a real-time update module.

In Example 21, the subject matter of any of Examples 1-20 includes, wherein dynamically generating the prompt includes the capability to incorporate real-time environmental data that may affect the patient's session (e.g., through an environmental data integration module).

In Example 22, the subject matter of any of Examples 1-21 includes, wherein dynamically generating the prompt includes the option to manually adjust the generated prompt by a healthcare provider before it is provided to the LLM through a manual adjustment interface.

Example 23 is a computer-implemented method for prioritizing input data in a digital therapy platform for generating personalized feedback, comprising: collecting a plurality of data points related to a patient's session; applying a set of hierarchical rules to the collected data points to determine their relative importance; generating a structured prompt for a large language model (LLM) based on the prioritized data points; instructing the LLM to generate feedback that emphasizes the most significant data points as determined by the hierarchical rules; and delivering the generated feedback to the patient.

In Example 24, the subject matter of Example 23 includes, wherein the data points include at least one of the patient's range of motion, exercise completion rate, movement accuracy, or adherence to prescribed exercises.

In Example 25, the subject matter of any of Examples 23-24 includes, wherein the hierarchical rules are based on clinical guidelines established by healthcare professionals to ensure the feedback is clinically relevant.

In Example 26, the subject matter of any of Examples 23-25 includes, wherein generating the structured prompt further comprises incorporating patient-specific goals to tailor the feedback.

In Example 27, the subject matter of any of Examples 23-26 includes, wherein the LLM is further configured to adapt the generated feedback based on the patient's historical therapy data and previous feedback responses.

In Example 28, the subject matter of any of Examples 23-27 includes, wherein the feedback is delivered to the patient in real-time immediately following the completion of an exercise during the session.

In Example 29, the subject matter of any of Examples 23-28 includes, wherein the feedback is delivered in a format selected from the group consisting of text, audio, and visual cues.

In Example 30, the subject matter of any of Examples 23-29 includes, wherein the feedback includes motivational elements designed to encourage the patient to continue their therapy regimen.

In Example 31, the subject matter of any of Examples 23-30 includes, wherein the feedback is personalized further based on environmental factors affecting the session, as detected by the digital therapy platform.

In Example 32, the subject matter of any of Examples 23-31 includes, wherein the feedback is stored in a patient profile within the digital therapy platform for subsequent review by a healthcare provider.

Example 33 is a computer-implemented method for providing real-time audio feedback in a digital therapy environment, the method comprising: capturing, using a motion tracking module, real-time performance data of a patient during a session; generating, using a large language model (LLM), textual feedback based on the performance data; converting, by at least one processor, the textual feedback into audio feedback; and presenting the audio feedback to the patient immediately following an exercise.

In Example 34, the subject matter of Example 33 includes, wherein capturing real-time performance data includes utilizing sensors selected from the group consisting of accelerometers, gyroscopes, and cameras.

In Example 35, the subject matter of any of Examples 33-34 includes, incorporating, by at least one processor, historical data and patient-specific goals into the textual feedback.

In Example 36, the subject matter of any of Examples 33-35 includes, wherein the LLM is fine-tuned by at least one processor on a dataset comprising examples of sessions and associated feedback to improve its performance on generating personalized feedback.

In Example 37, the subject matter of any of Examples 33-36 includes, selecting, by at least one processor, from a range of voices and languages for the text-to-speech conversion to customize the audio feedback based on patient preferences.

In Example 38, the subject matter of any of Examples 33-37 includes, wherein presenting the audio feedback includes utilizing an output device that is part of a wearable device worn by the patient.

In Example 39, the subject matter of any of Examples 33-38 includes, adjusting, by at least one processor, the content of the textual feedback based on real-time environmental factors detected during the session.

In Example 40, the subject matter of any of Examples 33-39 includes, applying, by at least one processor, a set of hierarchical rules to prioritize certain types of performance data over others when generating the textual feedback.

In Example 41, the subject matter of any of Examples 33-40 includes, receiving and incorporating, by at least one processor, real-time input from a healthcare provider into the textual feedback.

In Example 42, the subject matter of any of Examples 33-41 includes, facilitating, by at least one processor in communication with a user interface, interaction with the system by the patient to provide input regarding the audio feedback.

In Example 43, the subject matter of any of Examples 33-42 includes, storing, by at least one processor in communication with a data storage module, the real-time performance data and generated feedback for subsequent analysis and review by healthcare providers.

Example 44 is a computer-implemented method for providing an adaptive conversational interface in a digital therapy platform, the method comprising: receiving natural language queries from a patient; interpreting, using a large language model (LLM), the queries and accessing therapy-related data; generating one or more or more natural language responses to the queries using the LLM; and presenting the natural language responses to the patient, thereby facilitating a conversational interaction.

In Example 45, the subject matter of Example 44 includes, wherein the natural language queries from the patient include inquiries about their therapy progress or instructions for therapeutic exercises.

In Example 46, the subject matter of any of Examples 44-45 includes, wherein the therapy-related data accessed includes at least one of the patient's historical therapy data, current therapy plan, or personalized therapy goals.

In Example 47, the subject matter of any of Examples 44-46 includes, wherein the LLM is further configured by at least one processor to be fine-tuned on a dataset comprising therapy-specific dialogues and patient interactions.

In Example 48, the subject matter of any of Examples 44-47 includes, adapting, by at least one processor, the natural language responses based on the patient's therapy history and preferences.

In Example 49, the subject matter of any of Examples 44-48 includes, wherein an output module includes a display screen, speaker, or a combination thereof for presenting the responses.

In Example 50, the subject matter of any of Examples 44-49 includes, customizing, by at least one processor, the conversational interface based on the patient's language preferences and accessibility needs.

In Example 51, the subject matter of any of Examples 44-50 includes, wherein a response generation module is further configured by at least one processor to generate responses that include motivational messages tailored to the patient's therapy session.

In Example 52, the subject matter of any of Examples 44-51 includes, storing, by at least one processor, the conversational interactions in a patient profile within the digital therapy platform for subsequent review and analysis.

In Example 53, the subject matter of any of Examples 44-52 includes, updating, by at least one processor, the therapy-related data in real-time based on the patient's input and the conversational interactions.

In Example 54, the subject matter of any of Examples 44-53 includes, wherein the conversational interface is further configured by at least one processor to support multi-language interactions, allowing the system to communicate with patients in their preferred language.

Example 55 is a method for fine-tuning a large language model (LLM) for use in a digital therapy platform, comprising: identifying, by at least one processor, a set of therapy-specific feedback tasks; providing the LLM with a dataset comprising examples of therapy sessions and associated feedback; training the LLM on the set of therapy-specific feedback tasks to generate a fined-tuned LLM; and integrating the fine-tuned LLM into the digital therapy platform to generate personalized motivational messages for patients.

In Example 56, the subject matter of Example 55 includes, wherein identifying the set of therapy-specific feedback tasks includes analyzing common therapeutic goals and challenges encountered by patients during therapy sessions.

In Example 57, the subject matter of any of Examples 55-56 includes, wherein the dataset further comprises patient demographic information, therapy outcomes, and patient feedback to enhance the personalization of the LLM's responses.

In Example 58, the subject matter of any of Examples 55-57 includes, wherein training the LLM includes using machine learning techniques selected from the group consisting of supervised learning, unsupervised learning, and reinforcement learning.

In Example 59, the subject matter of any of Examples 55-58 includes, evaluating, by at least one processor, the performance of the fine-tuned LLM using a validation set separate from the training dataset.

In Example 60, the subject matter of any of Examples 55-59 includes, wherein the personalized motivational messages are tailored to individual patient profiles, including their therapy history and personal therapy objectives.

In Example 61, the subject matter of any of Examples 55-60 includes, updating, by at least one processor, the fine-tuned LLM periodically with additional data collected from ongoing therapy sessions.

In Example 62, the subject matter of any of Examples 55-61 includes, wherein integrating the fine-tuned LLM into the digital therapy platform includes configuring the system to use the LLM in real-time during therapy sessions.

In Example 63, the subject matter of any of Examples 55-62 includes, generating, by at least one processor, a user interface within the digital therapy platform that allows healthcare providers to interact with the fine-tuned LLM.

In Example 64, the subject matter of any of Examples 55-63 includes, wherein the fine-tuned LLM is configured, by at least one processor, to generate feedback in multiple languages to accommodate patients of diverse linguistic backgrounds.

In Example 65, the subject matter of any of Examples 1-22 includes, wherein causing the presentation of the personalized motivational message to the patient comprises causing presentation of the personalized motivational message at a user device of the patient that executes a digital therapy application, the user device of the patient including or being communicatively coupled to one or more sensors used to obtain motion data from the patient during the session, the real-time performance data being at least partially based on the motion data.

In Example 66, the subject matter of Example 65 includes, wherein the method comprises using the one or more sensors to obtain the motion data from the patient during the session.

In Example 67, the subject matter of Example 65 or 66 includes, wherein the method comprises generating the real-time performance data based on the motion data.

In Example 68, the subject matter of any of Examples 1-22 includes, wherein the historical data comprises at least one of patient-specific historical data related to historical performance of the patient or population-based historical data related to historical performance of a group of patients.

In Example 69, the subject matter of any of Examples 1-22 includes, wherein the personalized message comprises a personalized cue for performing an exercise during the session, the personalized cue being presented to the patient in real-time based on an analysis of the real-time performance data.

Example 70 is at least one non-transitory machine-readable medium including instructions that, when executed by processing circuitry, cause the processing circuitry to perform operations to implement any of Examples 1-69.

Example 71 is an apparatus comprising means to implement any of Examples 1-69.

Example 72 is a system to implement any of Examples 1-69.

Example 73 is a method to implement any of Examples 1-69.

Although specific examples are described herein, it will be evident that various modifications and changes may be made to these examples without departing from the broader spirit and scope of the disclosure. Accordingly, the specification and drawings are to be regarded in an illustrative rather than a restrictive sense. The accompanying drawings that form a part hereof show by way of illustration, and not of limitation, specific examples in which the subject matter may be practiced. The examples illustrated are described in sufficient detail to enable those skilled in the art to practice the teachings disclosed herein. Other examples may be utilized and derived therefrom, such that structural and logical substitutions and changes may be made without departing from the scope of this disclosure. This detailed description, therefore, is not to be taken in a limiting sense, and the scope of various examples is defined only by the appended claims, along with the full range of equivalents to which such claims are entitled.

Such examples of the inventive subject matter may be referred to herein, individually or collectively, by the term "example" merely for convenience and without intending to voluntarily limit the scope of this application to any single example or concept if more than one is in fact disclosed. Thus, although specific examples have been illustrated and described herein, it should be appreciated that any arrangement calculated to achieve the same purpose may be substituted for the specific examples shown. This disclosure is intended to cover any and all adaptations or variations of various examples. Combinations of the above examples, and other examples not specifically described herein, will be apparent to those of skill in the art upon reviewing the above description.

Some portions of the subject matter discussed herein may be presented in terms of algorithms or symbolic representations of operations on data stored as bits or binary digital signals within a machine memory (e.g., a computer memory). Such algorithms or symbolic representations are examples of techniques used by those of ordinary skill in the data processing arts to convey the substance of their work to others skilled in the art. As used herein, an "algorithm" is a self-consistent sequence of operations or similar processing leading to a desired result. In this context, algorithms and operations involve physical manipulation of physical quantities. Typically, but not necessarily, such quantities may take the form of electrical, magnetic, or optical signals capable of being stored, accessed, transferred, combined, compared, or otherwise manipulated by a machine. It is convenient at times, principally for reasons of common usage, to refer to such signals using words such as "data," "content," "bits," "values," "elements," "symbols," "characters," "terms," "numbers," "numerals," or the like. These words, however, are merely convenient labels and are to be associated with appropriate physical quantities.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or any suitable combination thereof), registers, or other machine components that receive, store, transmit, or display information. Furthermore, unless specifically stated otherwise, the terms "a" and "an" are herein used, as is common in patent documents, to include one or more than one instance.

Unless the context clearly requires otherwise, throughout the description and the claims, the words "comprise," "comprising," and the like are to be construed in an inclusive sense, as opposed to an exclusive or exhaustive sense, e.g., in the sense of "including, but not limited to." As used herein, the terms "connected," "coupled," or any variant thereof means any connection or coupling, either direct or indirect, between two or more elements; the coupling or connection between the elements can be physical, logical, or a combination thereof. Additionally, the words "herein," "above," "below," and words of similar import, when used in this application, refer to this application as a whole and not to any particular portions of this application. Where the context permits, words using the singular or plural number may also include the plural or singular number, respectively. The word "or" in reference to a list of two or more items, covers all of the following interpretations of the word: any one of the items in the list, all of the items in the list, and any combination of the items in the list.

Although some examples, such as those depicted in the drawings, may include a particular sequence of operations, the sequence may be altered without departing from the scope of the present disclosure. For example, some of the operations depicted may be performed in parallel or in a different sequence that does not materially affect the functions as described in the examples. In other examples, different components of an example device or system that implements an example method may perform functions at substantially the same time or in a specific sequence. The term "operation" may be used to refer to elements in the drawings of this disclosure for ease of reference and it will be appreciated that each "operation" may identify one or more operations, processes, actions, or steps, and may be performed by one or multiple components.

As used in this disclosure, the term "machine learning model" (or simply "model") may refer to a single, stand-alone model, or a combination of models. The term may also refer to a system, component or module that includes a machine learning model together with one or more supporting or supplementary components that do not necessarily perform machine learning tasks.

What is claimed is:

1. A computer-implemented method for generating personalized messages in a digital therapy platform, the method comprising:
rendering and displaying, at a user device of a patient, a user interface of the digital therapy platform to present instructions for performing an exercise involving one or more body parts;
capturing, by one or more sensors associated with the user device, motion data for the patient during a session of the digital therapy platform while the patient performs the exercise and while maintaining display of the user interface;
processing, by at least one processor, the motion data while the session is in progress to track motion of the one or more body parts and generate real-time performance data for the patient;
displaying, while the session is in progress, at least one of the motion data or the real-time performance data in the user interface;
automatically accessing, by the at least one processor, input data comprising at least one of the real-time performance data or historical data associated with the patient;
automatically and dynamically generating, by the at least one processor, a prompt for a Large Language Model (LLM) based on the input data, the generating of the prompt for the LLM comprising generating a prompt data structure and updating at least part of the prompt data structure in real-time, while the session is in progress, based on at least one of the real-time performance data or the historical data;
automatically generating, using the LLM, a personalized message based on the prompt; and
automatically causing real-time presentation of the personalized message to the patient, the real-time presentation comprising at least one of:
transmitting, by audio hardware of the user device, audio output to deliver the personalized message: or
displaying the personalized message in the user interface.

2. The method of claim 1, wherein the real-time performance data includes quantitative metrics comprising at least one of range of motion, movement of pelvic floor muscles, exercise completion, or movement accuracy.

3. The method of claim 1, wherein the historical data comprises at least one of quantitative metrics indicative of historical performance from a previous session, information describing a goal of the patient, or information describing a baseline condition of the patient.

4. The method of claim 1, wherein dynamically generating the prompt further comprises employing a rules-based engine to prioritize a first type of the input data over a second type of the input data based on quantitative significance.

5. The method of claim 1, wherein the personalized message includes feedback on progress of the patient relative to a goal.

6. The method of claim 1, further comprising:
detecting completion of the exercise, wherein the personalized message is generated in real-time in response to detecting the completion of the exercise.

7. The method of claim 1, further comprising receiving and responding, via the LLM, to a follow-up question from the patient in natural language based on a contextual understanding of the session.

8. The method of claim 1, wherein the LLM is fine-tuned based on a dataset comprising examples of sessions.

9. The method of claim 1, wherein the personalized message is adapted based on an analysis of performance trends of the patient observed over multiple sessions.

10. The method of claim 1, wherein the digital therapy platform is configured to store the personalized message for review by a healthcare provider in a structured database.

11. The method of claim 1, wherein the digital therapy platform is configured to adjust at least one of difficulty or intensity of subsequent exercises based on an analysis of the personalized message.

12. The method of claim 1, wherein the personalized message comprises a personalized cue for performing an exercise during the session, the personalized cue being presented to the patient in real-time based on an analysis of the real-time performance data.

13. The method of claim 1, wherein dynamically generating the prompt includes utilizing one or more machine learning algorithms to determine the prompt data structure based on a combination of the real-time performance data and the historical data.

14. The method of claim 1, wherein the historical data comprises at least one of patient-specific historical data related to historical performance of the patient or population-based historical data related to historical performance of a group of patients.

15. The method of claim 1, further comprising:
receiving user input via the user device of the patient; and
in response to receiving the user input, automatically adjusting one or more subsequent exercises of the session.

16. The method of claim 1, wherein the prompt data structure comprises a base prompt structure, and wherein the dynamic generation of the prompt comprises:
identifying a scenario type from among a plurality of scenario types;
generating the base prompt structure based on the scenario type; and
dynamically integrating at least some of the input data into the base prompt structure.

17. The method of claim 1, wherein the prompt data structure comprises:
a system prompt that includes an instruction;
a scenario descriptor; and
a user prompt that includes at least some of the input data.

18. The method of claim 1, wherein the one or more sensors comprise a camera of the user device, the capturing of the motion data comprises capturing, by the camera, images of the one or more body parts while the patient performs the exercise, and the processing of the motion data comprises processing the images in real-time using one or more computer vision algorithms to track the motion of the one or more body parts appearing in the images while the session is in progress.

19. A system comprising:
at least one processor; and
at least one memory storing instructions that, when executed by the at least one processor, configure the system to perform operations comprising:
rendering and displaying, at a user device of a patient, a user interface of a digital therapy platform to present instructions for performing an exercise involving one or more body parts;
capturing, by one or more sensors associated with the user device, motion data for the patient during a session of the digital therapy platform while the patient performs the exercise and while maintaining display of the user interface;
processing the motion data while the session is in progress to track motion of the one or more body parts and generate real-time performance data for the patient;
displaying, while the session is in progress, at least one of the motion data or the real-time performance data in the user interface;
automatically accessing input data comprising at least one of the real-time performance data or historical data associated with the patient;
automatically and dynamically generating a prompt for a Large Language Model (LLM) based on the input data, the generating of the prompt for the LLM comprising generating a prompt data structure and updating at least part of the prompt data structure in real-time, while the session is in progress, based on at least one of the real-time performance data or the historical data;
automatically generating, using the LLM, a personalized message based on the prompt; and
automatically causing real-time presentation of the personalized message to the patient, the real-time presentation comprising at least one of:
transmitting, by audio hardware of the user device, audio output to deliver the personalized message: or
displaying the personalized message in the user interface.

20. A non-transitory machine-readable storage medium, the machine-readable storage medium including instructions that when executed by a computer system, cause the computer system to perform operations comprising:
rendering and displaying, at a user device of a patient, a user interface of a digital therapy platform to present instructions for performing an exercise involving one or more body parts;
capturing, one or more sensors associated with the user device, motion data for the patient during a session of the digital therapy platform while the patient performs the exercise and while maintaining display of the user interface;
processing the motion data while the session is in progress to track motion of the one or more body parts and generate real-time performance data for the patient;
displaying, while the session is in progress, at least one of the motion data or the real-time performance data in the user interface;
automatically accessing input data comprising at least one of the real-time performance data or historical data associated with the patient;
automatically and dynamically generating a prompt for a Large Language Model (LLM) based on the input data, the generating of the prompt for the LLM comprising generating a prompt data structure and updating at least part of the prompt data structure in real-time, while the session is in progress, based on at least one of the real-time performance data or the historical data;
automatically generating, using the LLM, a personalized message based on the prompt; and
automatically causing real-time presentation of the personalized message to the patient, the real-time presentation comprising at least one of:
transmitting, by audio hardware of the user device, audio output to deliver the personalized message: or
displaying the personalized message in the user interface.

\* \* \* \* \*

UNITED STATES PATENT AND TRADEMARK OFFICE
CERTIFICATE OF CORRECTION

PATENT NO. : 12,397,198 B1  
APPLICATION NO. : 18/585355  
DATED : August 26, 2025  
INVENTOR(S) : Bento et al.

Page 1 of 1

It is certified that error appears in the above-identified patent and that said Letters Patent is hereby corrected as shown below:

In the Claims

In Column 61, Line 57, in Claim 1, delete "of;" and insert --of:-- therefor

In Column 61, Line 59, in Claim 1, delete "message:" and insert --message;-- therefor In Column 64, Line 2, in Claim 19, delete "message:" and insert --message;-- therefor In Column 64, Line 14, in Claim 20, after "capturing,", insert --by--

In Column 64, Line 40, in Claim 20, delete "message:" and insert --message;-- therefor Signed and Sealed this  
Third Day of February, 2026

John A. Squires  
*Director of the United States Patent and Trademark Office*